United States Patent
Zhang et al.

(10) Patent No.: US 9,915,663 B2
(45) Date of Patent: *Mar. 13, 2018

(54) THYROGLOBULIN QUANTITATION BY MASS SPECTROSCOPY

(71) Applicant: Quest Diagnostics Investments Incorporated, Wilmington, DE (US)

(72) Inventors: Yanni Zhang, Mission Viejo, CA (US); Nigel J. Clarke, Oceanside, CA (US); Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,805

(22) Filed: Feb. 27, 2017

(65) Prior Publication Data

US 2017/0176452 A1    Jun. 22, 2017

Related U.S. Application Data

(63) Continuation of application No. 14/689,542, filed on Apr. 17, 2015, now Pat. No. 9,580,740, which is a continuation of application No. 14/031,678, filed on Sep. 19, 2013, now Pat. No. 9,012,394.

(60) Provisional application No. 61/703,721, filed on Sep. 20, 2012.

(51) Int. Cl.
*A61K 38/00* (2006.01)
*G01N 33/68* (2006.01)
*C12Q 1/37* (2006.01)

(52) U.S. Cl.
CPC .......... *G01N 33/6848* (2013.01); *C12Q 1/37* (2013.01); *G01N 33/6893* (2013.01); *G01N 2496/00* (2013.01); *G01N 2560/00* (2013.01); *G01N 2800/046* (2013.01); *G01N 2800/7028* (2013.01)

(58) Field of Classification Search
CPC .......... G01N 2333/47; G01N 2496/00; G01N 2560/00; G01N 2800/046; G01N 2800/7028; G01N 33/6848; G01N 33/6893; G01N 33/78; C12Q 1/37
See application file for complete search history.

(56) References Cited

U.S. PATENT DOCUMENTS

| | | | |
|---|---|---|---|
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koester | |
| 8,030,084 B2 | 10/2011 | Zhang et al. | |
| 8,455,259 B2 | 6/2013 | Zhang et al. | |
| 8,574,915 B2 | 11/2013 | Zhang et al. | |
| 9,012,394 B2 | 4/2015 | Zhang et al. | |
| 9,046,531 B2 | 6/2015 | Zhang et al. | |
| 9,140,695 B2* | 9/2015 | Kushnir | G01N 33/5306 |
| 9,580,740 B2* | 2/2017 | Zhang | G01N 33/6848 |
| 2004/0072251 A1 | 4/2004 | Anderson | |
| 2005/0064422 A1 | 3/2005 | Barnidge et al. | |
| 2006/0223188 A1 | 10/2006 | Soldin | |
| 2007/0105179 A1 | 5/2007 | Madson | |
| 2007/0224628 A1 | 9/2007 | Gordon et al. | |
| 2009/0042213 A1 | 2/2009 | Hoofnagle et al. | |
| 2012/0009614 A1 | 1/2012 | Zhang et al. | |

FOREIGN PATENT DOCUMENTS

| | | |
|---|---|---|
| WO | 2008027861 A1 | 3/2008 |
| WO | 2012111249 A1 | 8/2012 |

OTHER PUBLICATIONS

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Biemann K., "Mass Spectrometry of Peptides and Proteins," Annual Review of Biochemistry, 1992, vol. 61, pp. 977-1010.
Bourrel F., et al., "Immunoradiometric Assay of Thyroglobulin in Patients with Differentiated Thyroid Carcinomas: Need for Thyroglobulin Recovery Tests," Clinical Chemistry and Laboratory Medicine, 1998, vol. 36 (8), pp. 725-730.
Di Jeso B., et al., "Mixed-Disulfide Folding Intermediates between Thyroglobulin and Endoplasmic Reticulum Resident Oxidoreductases ERp57 and protein Disulfide Isomerase," Molecular and Cellular Biology, 2005, vol. 25 (22), pp. 9793-9805.
Dunn A.D., et al., "Tyrosine 130 is an Important Outer Ring Donor for Thyroxine Formation in Thyroglobulin," The Journal of Biological Chemistry, 1998, vol. 273 (39), pp. 25223-25229.
Dunn J.T., et al., "The Sites of Thyroid Hormone Formation in Rabbit Thyroglobulin," The Journal of Biological Chemistry, 1987, vol. 262 (35), pp. 16948-16952.
European Search Report for Application No. EP13185360, dated Jan. 22, 2014, 7 pages.
Extended European Search Report for Application No. PCT/US2013/060659, dated Mar. 21, 2016, 11 pages .
Final Office Action dated Aug. 1, 2016 for U.S. Appl. No. 14/726,957, filed Jun. 1, 2015.
Final Office Action dated Sep. 6, 2012 for U.S. Appl. No. 13/198,620, filed Aug. 4, 2011.
Final Office Action dated Jan. 25, 2011 for U.S. Appl. No. 12/001,076, filed Dec. 6, 2007.

(Continued)

*Primary Examiner* — Marcela M Cordero Garcia
(74) *Attorney, Agent, or Firm* — Quest Diagnostics, Inc.

(57) ABSTRACT

Provided are methods for determining the amount of thyroglobulin in a sample using various purification steps followed by mass spectrometry. The methods generally involve purifying thyroglobulin in a test sample, digesting thyroglobulin to form peptide T129, purifying peptide T129, ionizing peptide T129, detecting the amount of peptide T129 ion generated, and relating the amount of peptide T129 ion to the amount of thyroglobulin originally present in the sample.

11 Claims, 17 Drawing Sheets

(56) References Cited

OTHER PUBLICATIONS

Final Office Action dated Aug. 27, 2014 for U.S. Appl. No. 14/053,423, filed Oct. 14, 2013.
Final Office Action dated Oct. 27, 2010 for U.S. Appl. No. 12/001,076, filed Dec. 6, 2007.
Gentile F., et al., "Identification of Hormonogenic Tyrosines in Fragment 1218-1591 of Bovine Thyroglobulin by Mass Spectrometry. Hormonogenic Acceptor Tyr-1291 and Donor Tyr-1375," The Journal of Biological Chemistry, 1997, vol. 272 (1), pp. 639-646.
Hoofnagle A.N., et al., "Quantification of Thyroglobulin, a Low-Abundance Serum Protein, by Immunoaffinity Peptide Enrichment and Tandem Mass Spectrometry," Clinical Chemistry, 2008, vol. 54 (11), pp. 1796-1804.
International Preliminary Report on Patentability for Application No. PCT/US2008/085435, dated Jun. 8, 2010.
International Search Report and Written Opinion for Application No. PCT/US2013/60659, dated Dec. 23, 2013, 10 pages.
International Search Report for Application No. PCT/US08/85435, dated Apr. 22, 2009, 2 Pages.
Kim P.S., et al., "Folding and Assembly of Newly Synthesized Thyroblobulin Occurs in a Pre-Golgi Compartment," The Journal of Biological Chemistry, 1991, vol. 266 (19), pp. 12412-12418.
Kushnir M.M., et al., "High Sensitivity Measurement of Thyroglobulin in Serum in Presence of Anti-Thyroglobulin Autoantibodies," May 15, 2012. Retrieved from the Internet: URL:https://www.aruplab.com/Research&Development/resources/Posters/2012/Kushnir_ASMS_0512.pdf.
Kushnir M.M., et al., "Mass Spectrometry Based Method for Accurate Measurement of Thyroglobulin in the Presence of Anti-Thyroglobulin Autoantibodies," May 15, 2012. Retrieved from the Internet: URL:https://www.aruplab.com/Research&Development/resources/Posters/2013/Kushnir_END0_0613.pdf.
Kushnir M.M., et al., "Measurement of Thyroglobulin by Liquid Chromatography—Tandem Mass Spectrometry in Serum and Plasma in the Presence of Anti-thyroglobulin Autoantibodies," Clinical Chemistry, 2013, vol. 59(6), pp. 982-990.
"Screenshot of Google page", Mar. 10, 2016, XP055257300, Retrieved from the Internet: URL: www.google.com.
Learmonth M., et al., "Protein Identification by In-Gel Digestion and Mass Spectrometric Analysis," in: The Proteomics Protocols Handbook, 2005, Chapter 30, Walker J.M., ed., Humana Press, pp. 311-314.
Luo J.L., et al., "Diagnostic Value of Combing TG, TGAb and Cervical Ultrasonic Examination in the Recurrence or Metastasis Lesion of Differentiated Thyroid Carcinoma after Treatment," Chinese Journal of Clinicians (Electronic Edition), 2012, vol. 6 (3), pp. 580-583.
Mann M., et al., "Analysis of Proteins and Proteomes by Mass Spectrometry," Annual Review of Biochemistry, 2001, vol. 70, pp. 437-473.
Mann M., "Functional and Quantitative Proteomics Using SILAC," Nature Reviews Molecular Cell Biology, 2006, vol. 7 (12), pp. 952-958.
Meikla.W., et al., "Diagnosis and Management of Thyroid Nodules and Cancer Focus on Thyroglobulin; Thyroglobulin and Thyroid Cancer: Part 2 of Presentation: Analytical Method and Performance", Nov. 16, 2012. Retrieved from the Internet: URL:http://arup.utah.edu/media/thyroidglobulin/thyroid.cancer.pgr.final.pdf.
Merchant M., et al., "Recent Advancements in Surface-Enhanced Laser Desorption/Ionization—Time of Flight-Mass Spectrometry," Electrophoresis, 2000, vol. 21 (6), pp. 1164-1167.
Non-Final Office Action dated Jan. 12, 2016 for U.S. Appl. No. 14/726,957, filed Jun. 1, 2015.
Non-Final Office Action dated Jun. 19, 2014 for U.S. Appl. No. 14/031,678, filed Sep. 19, 2013.
Non-Final Office Action dated Jan. 22, 2016 for U.S. Appl. No. 14/063,956, filed Oct. 25, 2013.
Non-Final Office Action dated Dec. 23, 2013 for U.S. Appl. No. 14/053,423, filed Oct. 14, 2013.
Non-Final Office Action dated Apr. 27, 2016 for U.S. Appl. No. 14/689,542, filed Apr. 14, 2015.
Non-Final Office Action dated Apr. 28, 2010 for U.S. Appl. No. 12/001,076, filed Dec. 6, 2007.
Non-Final Office Action dated Nov. 30, 2011 for U.S. Appl. No. 13/198,620, filed Aug. 4, 2011.
Olsen J.V., et al., "Trypsin Cleaves Exclusively C-Terminal to Arginine and Lysine Residues," Molecular & Cellular Proteomics, 2004, vol. 3 (6), pp. 608-614.
Persoon A.C., et al., "Clinical Utility of an Automated Immunochemiluminometric Thyroglobulin Assay in Differentiated Thyroid Carcinoma," Clinical Chemistry, 2006, vol. 52 (4), pp. 686-691.
Persoon A.C., et al., "Thyroblobulin (Tg) Recovery Testing with Quantitative Tg Antibody Measurement for Determining Interference in Serum Tg Assays in Difffferentiated Thyroid Carcinoma," Clinical Chemistry, 2006, vol. 52 (6), pp. 1196-1199.
Robb D.B., et al., "Atmospheric Pressure Photoionization: An Ionization Method for Liquid Chromatography—Mass Spectrometry," Analytical Chemistry, 2000, vol. 72 (15), pp. 3653-3659.
Salek, "Analysis of Thyroblobulin Iodination by Tandem Mass Spectrometry Using Immonium Ions of Monoiodo—and Diiodo-Tyrosine," Proteomics, 2005, vol. 5 (2), pp. 351-353.
Salm P., et al., "The Quantification of Sirolimus by High-Performance Liquid Chromatography—Tandem Mass Spectrometry and Microparticle Enzyme Immunoassay in Renal Transplant Recipients," Clinical Therapeutics, 2000, vol. 22 Suppl B, pp. B71-B85.
Spencer C.A., et al., "Detection of Residual and Recurrent Differentiated Thyroid Carcinoma by Serum Thyroglobulin Measurement," Thyroid, 1999, vol. 9 (5), pp. 435-441.
Spencer C.A., et al., "Thyroglobulin Measurement Techniques, Clinical Benefits, and Pitfalls," Endocrinology Metabolism Clinics of North America , 1995, vol. 24 (4), pp. 841-863.
Steen H., et al., "The ABC's (and XYZ's) of Peptide Sequencing," Nature Reviews Molecular Cell Biology, 2004, vol. 5 (9), pp. 699-711.
Supplementary European Search Report for Application No. EP08860014, dated Jan. 28, 2011, 5 pages.
Tang X.J., et al., "An Investigation of Fragmentation Mechanisms of Doubly Protonated Tryptic Peptides," Rapid Communications in Mass Spectrometry, 1992, vol. 6 (11), pp. 651-677.
Taylor P.J., et al., "Simultaneous Quantification of Tacrolimus and Sirolimus in Human Blood, by High-Performance Liquid Chromatography—Tandem Mass Spectrometry," Therapeutic Drug Monitoring, 2000, vol. 22 (5), pp. 608-612.
Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.
Written Opinion for Application No. PCT/US08/85435, dated Apr. 22, 2009, 5 Pages.
Final Office Action dated Sep. 25, 2017 for U.S. Appl. No. 14/726,957, filed Jun. 1, 2015.
Guo-Zhong JI, et al., "Clinical Test Diagnosis and Resolution" Jan. 2011, pp. 335-336.
Non-Final Office Action dated Mar. 13, 2017 for U.S. Appl. No. 14/726,957, filed Jun. 1, 2015.

* cited by examiner

P01266 Sequence (SEQ ID NO: 3)
MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHCVTDCQRNEAGLQCDQNGQYRASQKDRGSGKAFCVDGEGRRLPWWETEAPL
EDSQCLMMQKFEKVPESKVIFDANAPVAVRSKVPDSEFPVMQCLTDCTEDEACSFFTVST
TEPEISCDFYAWTSDNVACMTSDQKRDALGNSKATSFGSLRCQVKVRSHGQDSPAVYLKK
GQGSTTTLQKRFEPTGFQNMLSGLYNPIVFSASGANLTDAHLFCLLACDRDLCCDGFVLT
QVQGGAIICGLLSSPSVLLCNVKDWMDPSEAWANATCPGVTYDQESHQVILRLGDQEFIK
SLTPLEGTQDTFTNFQQVYLWKDSDMGSRPESMGCRKDTVPRPASPTEAGLTTELFSPVD
LNQVIVNGNQSLSSQKHWLFKHLFSAQQANLWCLSRCVQEHSFCQLAEITESASLYFTCT
LYPEAQVCDDIMESNAQGCRLILPQMPKALFRKKVILEDKVKNFYTRLPFQKLMGISIRN
KVPMSEKSISNGFFECERRCDADPCCTGFGFLNVSQLKGGEVTCTLNSLGIQMCSEENG
GAWRILDCGSPDIEVHTYPFGWYQKPIAQNNAPSFCPLVVLPSLTEKVSLDSWQSLALSS
VVVDPSIRHFDVAHVSTAATSNFSAVRDLCLSECSQHEACLITTLQTQPGAVRCMFYADT
QSCTHSLQGQNCRLLLREEATHIYRKPGISLLSYEASVPSVPISTHGRLLGRSQAIQVGT
SWKQVDQFLGVPYAAPPLAERRFQAPEPLNWTGSWDASKPRASCWQPGTRTSTSPGVSED
CLYLNVFIPQNVAPNASVLVFFHNTMDREESEGWPAIDGSFLAAVGNLIVVTASYRVGVF
GFLSSGSGEVSGNWGLLDQVAALTWVQTHIRGFGGDPRRVSLAADRGGADVASIHLLTAR
ATNSQLFRRAVLMGGSALSPAAVISHERAQQQAIALAKEVSCPMSSSQEVVSCLRQKPAN
VLNDAQTKLLAVSGPFHYWGPVIDGHFLREPPARALKRSLWVEVDLLIGSSQDDGLINRA
KAVKQFEESRGRTSSKTAFYQALQNSLGGEDSDARVEAAATWYYSLEHSTDDYASFSRAL
ENATRDYFIICPIIDMASAWAKRARGNVFMYHAPENYGHGSLELLADVQFALGLPFYPAY
EGQFSLEEKSLSLKIMQYFSHFIRSGNPNYPYEFSRKVPTFATPWPDFVPRAGGENYKEF
SELLPNRQGLKKADCSFWSKYISSLKTSADGAKGGQSAESEEEELTAGSGLREDLLSLQE
PGSKTYSK

FIG. 11

P01266-2 Isoform 2 Sequence (SEQ ID NO: 4)
```
>sp_vs|P01266-2|THYG_HUMAN Isoform 2 of P01266 - Homo sapiens (Human)
MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHLMQKFEKVPESKVIFDANAPVAVRSKVPDSEFPVMQCLTDCTEDEACSFFT
VSTTEPEISCDFYAWTSDNVACMTSDQKRDALGNSKATSFGSLRCQVKVRSHGQDSPAVY
LKKGQGSTTTLQKRFEPTGFQNMLSGLYNPIVFSASGANLTDAHLFCLLACDRDLCCDGF
VLTQVQGGAIICGLLSSPSVLLCNVKDWMDPSEAWANATCPGVTYDQESHQVILRLGDQE
FIKSLTPLEGTQDTFTNFQQVYLWKDSDMGSRPESMGCRKDTVPRPASPTEAGLTTELFS
PVDLNQVIVNGNQSLSSQKHWLFKHLFSAQQANLWCLSRCVQEHSFCQLAEITESASLYF
TCTLYPEAQVCDDIMESNAQGCRLILPQMPKALFRKKVILEDKVKNFYTRLPFQKLMGIS
IRNKVPMSEKSISNGFFECERRCDADPCCTGFGFLNVSQLKGGEVTCLTLNSLGIQMCSE
ENGGAWRILDCGSPDIEVHTYPFGWYQKPIAQNNAPSFCPLVVLPSLTEKVSLDSWQSLA
LSSVVVDPSIRHFDVAHVSTAATSNFSAVRDLCLSECSQHEACLITTLQTQPGAVRCMFY
ADTQSCTHSLQGQNCRLLLREEATHIYRKPGISLLSYEASVPSVPISTHGRLLGRSQAIQ
VGTSWKQVDQFLGVPYAAPPLAERRFQAPEPLNWTGSWDASKPRASCWQPGTRTSTSPGV
SEDCLYLNVFIPQNVAPNASVLVFFHNTMDREESEGWPAIDGSFLAAVGNLIVVTASYRV
GVFGFLSSGSGEVSGNWGLLDQVAALTWVQTHIRGFGGDPRRVSLAADRGGADVASIHLL
TARATNSQLFRRAVLMGGSALSPAAVISHERAQQQAIALAKEVSCPMSSSQEVVSCLRQK
PANVLNDAQTKLLAVSGPFHYWGPVIDGHFLREPPARALKRSLWVEVDLLIGSSQDDGLI
NRAKAVKQFEESRGRTSSKTAFYQALQNSLGGEDSDARVEAAATWYYSLEHSTDDYASFS
RALENATRDYFIICPIIDMASAWAKRARGNVFMYHAPENYGHGSLELLADVQFALGLPFY
PAYEGQFSLEEKSLSLKIMQYFSHFIRSGNPNYPYEFSRKVPTFATPWPDFVPRAGGENY
KEFSELLPNRQGLKKADCSFWSKYISSLKTSADGAKGGQSAESEEEELTAGSGLREDLLS
LQEPGSKTYSK
```

FIG. 12

Q59GF0 (Tg variant-Fragment) Sequence; SEQ ID NO: 5

>Q59GF0|Q59GF0_HUMAN Thyroglobulin variant (Fragment) - Homo sapiens (Human).

IPRKPISKRPVRPSLPRSPRCPLPFNASEVVGGTILCETISGPTGSAMQQCQLLCRQGSW
SVFPPGPLICSLESGRWESQLPQPRACQRPQLWQTIQTQGHFQLQLPPGKMCSADYAGLL
QTFQVFILDELTARGFCQIQVKTFGTLVSIPVCNNSSVQVGCLTRERLGVNVTWKSRLED
IPVASLPDLHDIERALVGKDLLGRFTDLIQSGSFQLHLDSKTFPAETIRFLQGDHFGTSP
RTWFGCSEGFYQVLTSEASQDGLGCVKCPEGSYSQDEECIPCPVGFYQEQAGSLACVPCP
VGRTTISAGAFSQTHCVTDCQRNEAGLQCDQNGQYRASQKDRGSGKAFCVDGEGRRLPWW
ETEAPLEDSQCLMMQKFEKVPESKVIFDANAPVAVRSKVPDSEFPVMQCLTDCTEDEACS
FFTVSTTEPEISCDFYAWTSDNVACMTSDQKRDALGNSKATSFGSLRCQVKVRSHGQDSP
AVYLKKGQGSTTTLQKRFEPTGFQNMLSGLYNPIVFSASGANLTDAHLFCLLACDRDLCC
DGFVLTQVQGGAIICGLLSSPSVLLCNVKDWMDPSEAWANATCPGVTYDQESHQVILRLG
DQEFIKSLTPLEGTQDTFTNFQQVYLWKDSDMGSRPESMGCRKNTVPRPASPTEAGLTTE
LFSPVDLNQVIVNGNQSLSSQKHWLFKHLFSAQQANLWCLSRCVQEHSFCQLAEITESAS
LYFTCTLYPEAQVCDDIMESNAQGCRLILPQMPKALFRKKVILEDKVKNFYTRLPFQKLT
GISIRNKVPMSEKSISNGFFECERRCDADPCCTGFGFLNVSQLKGGEVTCLTLNSLGIQM
CSEENGGAWRILDCGSPDIEVHTYPFGWYQKPIAQNNAPSFCPLVVLPSLTEKVSLDSWQ
SLALSSVVVDPSIRHFDVAHVSTAATSNFSAVRDLCLSECSQHEACLITTLQTQPGAVRC
MFYADTQSCTHSLQGQNCRLLLREEATHIYRKPGISLLSYEASVPSVPISTHGRLLGRSQ
AIQVGTSWKQVDQFLGVPYAAPPLAERRFQAPEPLNWTGSWDASKPRASCWQPGTRTSTS
PGVSEDCLYLNVFIPQNVAPNASVLVFFHNTMDREESEGWPAIDGSFLAAVGNLIVVTAS
YRVGVFGFLSSGSGEVSGNWGLLDQVAALTWVQTHIRGFGGDPRRVSLAADRGGADVASI
HLLTARATNSQLFRRAVLMGGSALSPAAVISHERAQQQAIALAKEVSCPMSSSQEVVSCL
RQKPANVLNDAQTKLLAVSGPFHYWGPVIDGHFLREPPARALKRSLWVEVDLLIGSSQDD
GLINRAKAVKQFEESQGRTSSKTAFYQALQNSLGGEDSDARVEAAATWYYSLEHSTDDYA
SFSRALENATRDYFIICPIIDMASAWAKRARGNVFMYHAPENYGHGSLELLADVQFALGL
PFYPAYEGQFSLEEKSLSLKIMQYFSHFIRSGNPNYPYEFSRKVPTFATPWPDFVPRAGG
ENYKEFSELLPNRQGLKKADCSFWSKYISSLKTSADGAKGGQSAESEEEELTAGSGLRED
LLSLQEPGSKTYSK

FIG. 13

SEQ ID NO: 3

|  | 10 | 20 | 30 | 40 | 50 | 60 |
|---|---|---|---|---|---|---|
|  | MALVLEIFTL | LASICWVSAN | IFEYQVDAQP | LRPCELQRET | AFLKQADYVP | QCAEDGSFQT |
|  | MALVLEIFTL | LASICWVSAN | IFEYQVDAQP | LRPCELQRET | AFLKQADYVP | QCAEDGSFQT |

SEQ ID NO: 4

|  | 70 | 80 | 90 | 100 | 110 | 120 |
|---|---|---|---|---|---|---|
|  | VQCQNDGRSC | WCVGANGSEV | LGSRQPGRPV | ACLSFCQLQK | QQILLSGYIN | STDTSYLPQC |
|  | VQCQNDGRSC | WCVGANGSEV | LGSRQPGRPV | ACLSFCQLQK | QQILLSGYIN | STDTSYLPQC |

|  | 130 | 140 | 150 | 160 | 170 | 180 |
|---|---|---|---|---|---|---|
|  | QDSGDYAPVQ | CDVQQVQCWC | VDAEGMEVYG | TRQLGRPKRC | PRSCEIRNRR | LLHGVGDKSP |
|  | QDSGDYAPVQ | CDVQQVQCWC | VDAEGMEVYG | TRQLGRPKRC | PRSCEIRNRR | LLHGVGDKSP |

|  | 190 | 200 | 210 | 220 | 230 | 240 |
|---|---|---|---|---|---|---|
|  | PQCSAEGEFM | PVQCKFVNTT | DMMIFDLVHS | YNRFPDAFVT | FSSFQRRFPE | VSGYCHCADS |
|  | PQCSAEGEFM | PVQCKFVNTT | DMMIFDLVHS | YNRFPDAFVT | FSSFQRRFPE | VSGYCHCADS |

|  | 250 | 260 | 270 | 280 | 290 | 300 |
|---|---|---|---|---|---|---|
|  | QGRELAETGL | ELLLDEIYDT | IFAGLDLPST | FTETTLYRIL | QRRFLAVQSV | ISGRFRCPTK |
|  | QGRELAETGL | ELLLDEIYDT | IFAGLDLPST | FTETTLYRIL | QRRFLAVQSV | ISGRFRCPTK |

|  | 310 | 320 | 330 | 340 | 350 | 360 |
|---|---|---|---|---|---|---|
|  | CEVERFTATS | FGHPYVPSCR | RNGDYQAVQC | QTEGPCWCVD | AQGKEMHGTR | QQGEPPSCAE |
|  | CEVERFTATS | FGHPYVPSCR | RNGDYQAVQC | QTEGPCWCVD | AQGKEMHGTR | QQGEPPSCAE |

|  | 370 | 380 | 390 | 400 | 410 | 420 |
|---|---|---|---|---|---|---|
|  | GQSCASERQQ | ALSRLYFGTS | GYFSQHDLFS | SPEKRWASPR | VARFATSCPP | TIKELFVDSG |
|  | GQSCASERQQ | ALSRLYFGTS | GYFSQHDLFS | SPEKRWASPR | VARFATSCPP | TIKELFVDSG |

|  | 430 | 440 | 450 | 460 | 470 | 480 |
|---|---|---|---|---|---|---|
|  | LLRPMVEGQS | QQFSVSENLL | KEAIRAIFPS | RGLARLALQF | TTNPKRLQQN | LFGGKFLVNV |
|  | LLRPMVEGQS | QQFSVSENLL | KEAIRAIFPS | RGLARLALQF | TTNPKRLQQN | LFGGKFLVNV |

FIG. 14A

SEQ ID NO: 3
(cont.)

```
            490        500        510        520        530        540
       GQFNLSGALG TRGTFNFSQF FQQLGLASFL NGGRQEDLAK PLSVGLDSNS STGTPEAAKK
       GQFNLSGALG TRGTFNFSQF FQQLGLASFL NGGRQEDLAK PLSVGLDSNS STGTPEAAKK
```

SEQ ID NO: 4
(cont.)

```
            550        560        570        580        590        600
       DGTMNKPTVG SFGFEINLQE NQNALKFLAS LLELPEFLLF LQHAISVPED VARDLGDVME
       DGTMNKPTVG SFGFEINLQE NQNALKFLAS LLELPEFLLF LQHAISVPED VARDLGDVME 610        620        630        640        650        660
       TVLSSQTCEQ TPERLFVPSC TTEGSYEDVQ CFSGECWCVN SWGKELPGSR VRGGQPRCPT
       TVLSSQTCEQ TPERLFVPSC TTEGSYEDVQ CFSGECWCVN SWGKELPGSR VRGGQPRCPT 670        680        690        700        710        720
       DCEKQRARMQ SLMGSQPAGS TLFVPACTSE GHFLPVQCFN SECYCVDAEG QAIPGTRSAI
       DCEKQRARMQ SLMGSQPAGS TLFVPACTSE GHFLPVQCFN SECYCVDAEG QAIPGTRSAI 730        740        750        760        770        780
       GKPKKCPTPC QLQSEQAFLR TVQALLSNSS MLPTLSDTYI PQCSTDGQWR QVQCNGPPEQ
       GKPKKCPTPC QLQSEQAFLR TVQALLSNSS MLPTLSDTYI PQCSTDGQWR QVQCNGPPEQ 790        800        810        820        830        840
       VFELYQRWEA QNKGQDLTPA KLLVKIMSYR EAASGNFSLF IQSLYEAGQQ DVFPVLSQYP
       VFELYQRWEA QNKGQDLTPA KLLVKIMSYR EAASGNFSLF IQSLYEAGQQ DVFPVLSQYP 850        860        870        880        890        900
       SLQDVPLAAL EGKRPQPREN ILLEPYLFWQ ILNGQLSQYP GSYSDFSTPL AHFDLRNCWC
       SLQDVPLAAL EGKRPQPREN ILLEPYLFWQ ILNGQLSQYP GSYSDFSTPL AHFDLRNCWC 910        920        930        940        950        960
       VDEAGQELEG MRSEPSKLPT CPGSCEEAKL RVLQFIRETE EIVSASNSSR FPLGESFLVA
       VDEAGQELEG MRSEPSKLPT CPGSCEEAKL RVLQFIRETE EIVSASNSSR FPLGESFLVA
```

FIG. 14B

SEQ ID NO: 3
(cont.)       970         980         990        1000        1010        1020
      KGIRLRNEDL  GLPPLFPPRE  AFAEQFLRGS  DYAIRLAAQS  TLSFYQRRRF  SPDDSAGASA
      KGIRLRNEDL  GLPPLFPPRE  AFAEQFLRGS  DYAIRLAAQS  TLSFYQRRRF  SPDDSAGASA
SEQ ID NO: 4
(cont.)      1030        1040        1050        1060        1070        1080
      LLRSGPYMPQ  CDAFGSWEPV  QCHAGTGHCW  CVDEKGGFIP  GSLTARSLQI  PQCPTTCEKS
      LLRSGPYMPQ  CDAFGSWEPV  QCHAGTGHCW  CVDEKGGFIP  GSLTARSLQI  PQCPTTCEKS 1090        1100        1110        1120        1130        1140
      RTSGLLSSWK  QARSQENPSP  KDLFVPACLE  TGEYARLQAS  GAGTWCVDPA  SGEELRPGSS
      RTSGLLSSWK  QARSQENPSP  KDLFVPACLE  TGEYARLQAS  GAGTWCVDPA  SGEELRPGSS 1150        1160        1170        1180        1190        1200
      SSAQCPSLCN  VLKSGVLSRR  VSPGYVPACR  AEDGGFSPVQ  CDQAQGSCWC  VMDSGEEVPG
      SSAQCPSLCN  VLKSGVLSRR  VSPGYVPACR  AEDGGFSPVQ  CDQAQGSCWC  VMDSGEEVPG
SEQ ID NO: 5                                                             IPRKPI 1210        1220        1230        1240        1250        1260
      TRVTGGQPAC  ESPRCPLPFN  ASEVVGGTIL  CETISGPTGS  AMQQCQLLCR  QGSWSVFPPG
      TRVTGGQPAC  ESPRCPLPFN  ASEVVGGTIL  CETISGPTGS  AMQQCQLLCR  QGSWSVFPPG
      SKRPVRPSLP  RSPRCPLPFN  ASEVVGGTIL  CETISGPTGS  AMQQCQLLCR  QGSWSVFPPG 1270        1280        1290        1300        1310        1320
      PLICSLESGR  WESQLPQPRA  CQRPQLWQTI  QTQGHFQLQL  PPGKMCSADY  ADLLQTFQVF
      PLICSLESGR  WESQLPQPRA  CQRPQLWQTI  QTQGHFQLQL  PPGKMCSADY  ADLLQTFQVF
      PLICSLESGR  WESQLPQPRA  CQRPQLWQTI  QTQGHFQLQL  PPGKMCSADY  AGLLQTFQVF 1330        1340        1350        1360        1370        1380
      ILDELTARGF  CQIQVKTFGT  LVSIPVCNNS  SVQVGCLTRE  RLGVNVTWKS  RLEDIPVASL
      ILDELTARGF  CQIQVKTFGT  LVSIPVCNNS  SVQVGCLTRE  RLGVNVTWKS  RLEDIPVASL
      ILDELTARGF  CQIQVKTFGT  LVSIPVCNNS  SVQVGCLTRE  RLGVNVTWKS  RLEDIPVASL

FIG. 14C

SEQ ID NO: 3, 4, 5 cont.
(top, middle, bottom, respectively)

```
           1390        1400        1410        1420        1430        1440
       PDLHDIERAL  VGKDLLGRFT  DLIQSGSFQL  HLDSKTFPAE  TIRFLQGDHF  GTSPRTWFGC
       PDLHDIERAL  VGKDLLGRFT  DLIQSGSFQL  HLDSKTFPAE  TIRFLQGDHF  GTSPRTWFGC
       PDLHDIERAL  VGKDLLGRFT  DLIQSGSFQL  HLDSKTFPAE  TIRFLQGDHF  GTSPRTWFGC 1450        1460        1470        1480        1490        1500
       SEGFYQVLTS  EASQDGLGCV  KCPEGSYSQD  EECIPCPVGF  YQEQAGSLAC  VPCPVGRTTI
       SEGFYQVLTS  EASQDGLGCV  KCPEGSYSQD  EECIPCPVGF  YQEQAGSLAC  VPCPVGRTTI
       SEGFYQVLTS  EASQDGLGCV  KCPEGSYSQD  EECIPCPVGF  YQEQAGSLAC  VPCPVGRTTI 1510        1520        1530        1540        1550        1560
       SAGAFSQTHC  VTDCQRNEAG  LQCDQNGQYR  ASQKDRGSGK  AFCVDGEGRR  LPWWETEAPL
       SAGAFSQTHL
       SAGAFSQTHC  VTDCQRNEAG  LQCDQNGQYR  ASQKDRGSGK  AFCVDGEGRR  LPWWETEAPL 1570        1580        1590        1600        1610        1620
       EDSQCLMMQK  FEKVPESKVI  FDANAPVAVR  SKVPDSEFPV  MQCLTDCTED  EACSFFTVST
              MQK  FEKVPESKVI  FDANAPVAVR  SKVPDSEFPV  MQCLTDCTED  EACSFFTVST
       EDSQCLMMQK  FEKVPESKVI  FDANAPVAVR  SKVPDSEFPV  MQCLTDCTED  EACSFFTVST 1630        1640        1650        1660        1670        1680
       TEPEISCDFY  AWTSDNVACM  TSDQKRDALG  NSKATSFGSL  RCQVKVRSHG  QDSPAVYLKK
       TEPEISCDFY  AWTSDNVACM  TSDQKRDALG  NSKATSFGSL  RCQVKVRSHG  QDSPAVYLKK
       TEPEISCDFY  AWTSDNVACM  TSDQKRDALG  NSKATSFGSL  RCQVKVRSHG  QDSPAVYLKK 1690        1700        1710        1720        1730        1740
       GQGSTTTLQK  RFEPTGFQNM  LSGLYNPIVF  SASGANLTDA  HLFCLLACDR  DLCCDGFVLT
       GQGSTTTLQK  RFEPTGFQNM  LSGLYNPIVF  SASGANLTDA  HLFCLLACDR  DLCCDGFVLT
       GQGSTTTLQK  RFEPTGFQNM  LSGLYNPIVF  SASGANLTDA  HLFCLLACDR  DLCCDGFVLT 1750        1760        1770        1780        1790        1800
       QVQGGAIICG  LLSSPSVLLC  NVKDWMDPSE  AWANATCPGV  TYDQESHQVI  LRLGDQEFIK
       QVQGGAIICG  LLSSPSVLLC  NVKDWMDPSE  AWANATCPGV  TYDQESHQVI  LRLGDQEFIK
       QVQGGAIICG  LLSSPSVLLC  NVKDWMDPSE  AWANATCPGV  TYDQESHQVI  LRLGDQEFIK
```

FIG. 14D

SEQ ID NO: 3, 4, 5 cont.
(top, middle, bottom, respectively)

```
          1810       1820       1830       1840       1850       1860
     SLTPLEGTQD TFTNFQQVYL WKDSDMGSRP ESMGCRKDTV PRPASPTEAG LTTELFSPVD
     SLTPLEGTQD TFTNFQQVYL WKDSDMGSRP ESMGCRKDTV PRPASPTEAG LTTELFSPVD
     SLTPLEGTQD TFTNFQQVYL WKDSDMGSRP ESMGCRKDTV PRPASPTEAG LTTELFSPVD 1870       1880       1890       1900       1910       1920
     LNQVIVNGNQ SLSSQKHWLF KHLFSAQQAN LWCLSRCVQE HSFCQLAEIT ESASLYFTCT
     LNQVIVNGNQ SLSSQKHWLF KHLFSAQQAN LWCLSRCVQE HSFCQLAEIT ESASLYFTCT
     LNQVIVNGNQ SLSSQKHWLF KHLFSAQQAN LWCLSRCVQE HSFCQLAEIT ESASLYFTCT 1930       1940       1950       1960       1970       1980
     LYPEAQVCDD IMESNAQGCR LILPQMPKAL FRKKVILEDK VKNFYTRLPF QKLMGISIRN
     LYPEAQVCDD IMESNAQGCR LILPQMPKAL FRKKVILEDK VKNFYTRLPF QKLMGISIRN
     LYPEAQVCDD IMESNAQGCR LILPQMPKAL FRKKVILEDK VKNFYTRLPF QKLMGISIRN 1990       2000       2010       2020       2030       2040
     KVPMSEKSIS NGFFECERRC DADPCCTGFG FLNVSQLKGG EVTCLTLNSL GIQMCSEENG
     KVPMSEKSIS NGFFECERRC DADPCCTGFG FLNVSQLKGG EVTCLTLNSL GIQMCSEENG
     KVPMSEKSIS NGFFECERRC DADPCCTGFG FLNVSQLKGG EVTCLTLNSL GIQMCSEENG 2050       2060       2070       2080       2090       2100
     GAWRILDCGS PDIEVHTYPF GWYQKPIAQN NAPSFCPLVV LPSLTEKVSL DSWQSLALSS
     GAWRILDCGS PDIEVHTYPF GWYQKPIAQN NAPSFCPLVV LPSLTEKVSL DSWQSLALSS
     GAWRILDCGS PDIEVHTYPF GWYQKPIAQN NAPSFCPLVV LPSLTEKVSL DSWQSLALSS 2110       2120       2130       2140       2150       2160
     VVVDPSIRHF DVAHVSTAAT SNFSAVRDLC LSECSQHEAC LITTLQTQPG AVRCMFYADT
     VVVDPSIRHF DVAHVSTAAT SNFSAVRDLC LSECSQHEAC LITTLQTQPG AVRCMFYADT
     VVVDPSIRHF DVAHVSTAAT SNFSAVRDLC LSECSQHEAC LITTLQTQPG AVRCMFYADT
```

FIG. 14E

SEQ ID NO: 3, 4, 5 cont.
(top, middle, bottom, respectively)

```
           2170       2180       2190       2200       2210       2220
     QSCTHSLQGQ NCRLLLREEA THIYRKPGIS LLSYEASVPS VPISTHGRLL GRSQAIQVGT
     QSCTHSLQGQ NCRLLLREEA THIYRKPGIS LLSYEASVPS VPISTHGRLL GRSQAIQVGT
     QSCTHSLQGQ NCRLLLREEA THIYRKPGIS LLSYEASVPS VPISTHGRLL GRSQAIQVGT 2230       2240       2250       2260       2270       2280
     SWKQVDQFLG VPYAAPPLAE RRFQAPEPLN WTGSWDASKP RASCWQPGTR TSTSPGVSED
     SWKQVDQFLG VPYAAPPLAE RRFQAPEPLN WTGSWDASKP RASCWQPGTR TSTSPGVSED
     SWKQVDQFLG VPYAAPPLAE RRFQAPEPLN WTGSWDASKP RASCWQPGTR TSTSPGVSED 2290       2300       2310       2320       2330       2340
     CLYLNVFIPQ NVAPNASVLV FFHNTMDREE SEGWPAIDGS FLAAVGNLIV VTASYRVGVF
     CLYLNVFIPQ NVAPNASVLV FFHNTMDREE SEGWPAIDGS FLAAVGNLIV VTASYRVGVF
     CLYLNVFIPQ NVAPNASVLV FFHNTMDREE SEGWPAIDGS FLAAVGNLIV VTASYRVGVF 2350       2360       2370       2380       2390       2400
     GFLSSGSGEV SGNWGLLDQV AALTWVQTHI RGFGGDPRRV SLAADRGGAD VASIHLLTAR
     GFLSSGSGEV SGNWGLLDQV AALTWVQTHI RGFGGDPRRV SLAADRGGAD VASIHLLTAR
     GFLSSGSGEV SGNWGLLDQV AALTWVQTHI RGFGGDPRRV SLAADRGGAD VASIHLLTAR 2410       2420       2430       2440       2450       2460
     ATNSQLFRRA VLMGGSALSP AAVISHERAQ QQAIALAKEV SCPMSSSQEV VSCLRQKPAN
     ATNSQLFRRA VLMGGSALSP AAVISHERAQ QQAIALAKEV SCPMSSSQEV VSCLRQKPAN
     ATNSQLFRRA VLMGGSALSP AAVISHERAQ QQAIALAKEV SCPMSSSQEV VSCLRQKPAN 2470       2480       2490       2500       2510       2520
     VLNDAQTKLL AVSGPFHYWG PVIDGHFLRE PPARALKRSL WVEVDLLIGS SQDDGLINRA
     VLNDAQTKLL AVSGPFHYWG PVIDGHFLRE PPARALKRSL WVEVDLLIGS SQDDGLINRA
     VLNDAQTKLL AVSGPFHYWG PVIDGHFLRE PPARALKRSL WVEVDLLIGS SQDDGLINRA 2530       2540       2550       2560       2570       2580
     KAVKQFEESR GRTSSKTAFY QALQNSLGGE DSDARVEAAA TWYYSLEHST DDYASFSRAL
     KAVKQFEESR GRTSSKTAFY QALQNSLGGE DSDARVEAAA TWYYSLEHST DDYASFSRAL
     KAVKQFEESR GRTSSKTAFY QALQNSLGGE DSDARVEAAA TWYYSLEHST DDYASFSRAL
```

FIG. 14F

SEQ ID NO: 3, 4, 5 cont.
(top, middle, bottom, respectively)

```
           2590       2600       2610       2620       2630       2640
     ENATRDYFII CPIIDMASAW AKRARGNVFM YHAPENYGHG SLELLADVQF ALGLPFYPAY
     ENATRDYFII CPIIDMASAW AKRARGNVFM YHAPENYGHG SLELLADVQF ALGLPFYPAY
     ENATRDYFII CPIIDMASAW AKRARGNVFM YHAPENYGHG SLELLADVQF ALGLPFYPAY 2650       2660       2670       2680       2690       2700
     EGQFSLEEKS LSLKIMQYFS HFIRSGNPNY PYEFSRKVPT FATPWPDFVP RAGGENYKEF
     EGQFSLEEKS LSLKIMQYFS HFIRSGNPNY PYEFSRKVPT FATPWPDFVP RAGGENYKEF
     EGQFSLEEKS LSLKIMQYFS HFIRSGNPNY PYEFSRKVPT FATPWPDFVP RAGGENYKEF 2710       2720       2730       2740       2750       2760
     SELLPNRQGL KKADCSFWSK YISSLKTSAD GAKGGQSAES EEEELTAGSG LREDLLSLQE
     SELLPNRQGL KKADCSFWSK YISSLKTSAD GAKGGQSAES EEEELTAGSG LREDLLSLQE
     SELLPNRQGL KKADCSFWSK YISSLKTSAD GAKGGQSAES EEEELTAGSG LREDLLSLQE

PGSKTYSK
     PGSKTYSK
     PGSKTYSK
```

FIG. 14G

SEQUENCE LISTING

```
<160> NUMBER OF SEQ ID NOS: 9

<210> SEQ ID NO 1
<211> LENGTH: 12
<212> TYPE: PRT
<213> ORGANISM: Homo sapiens

<400> SEQUENCE: 1

Val Ile Phe Asp Ala Asn Ala Pro Val Ala Val Arg
1               5                   10

<210> SEQ ID NO 2
<211> LENGTH: 24
<212> TYPE: PRT
<213> ORGANISM: Homo sapiens

<400> SEQUENCE: 2

Lys Val Pro Glu Ser Lys Val Ile Phe Asp Ala Asn Ala Pro Val Ala
1               5                   10                  15

Val Arg Ser Lys Val Pro Asp Ser
            20

<210> SEQ ID NO 3
<211> LENGTH: 2768
<212> TYPE: PRT
<213> ORGANISM: Homo sapiens

<400> SEQUENCE: 3

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
```

-continued

```
           65                  70                  75                  80
Leu Gly Ser Arg Gln Pro Gly Arg Pro Val Ala Cys Leu Ser Phe Cys
                    85                  90                  95

Gln Leu Gln Lys Gln Gln Ile Leu Leu Ser Gly Tyr Ile Asn Ser Thr
                100                 105                 110

Asp Thr Ser Tyr Leu Pro Gln Cys Gln Asp Ser Gly Asp Tyr Ala Pro
                115                 120                 125

Val Gln Cys Asp Val Gln Val Gln Cys Trp Cys Val Asp Ala Glu
130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Leu Leu His Gly Val Gly
                165                 170                 175

Asp Lys Ser Pro Pro Gln Cys Ser Ala Glu Gly Glu Phe Met Pro Val
                180                 185                 190

Gln Cys Lys Phe Val Asn Thr Thr Asp Met Met Ile Phe Asp Leu Val
                195                 200                 205

His Ser Tyr Asn Arg Phe Pro Asp Ala Phe Val Thr Phe Ser Ser Phe
210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Asp Glu
                245                 250                 255

Ile Tyr Asp Thr Ile Phe Ala Gly Leu Asp Leu Pro Ser Thr Phe Thr
                260                 265                 270

Glu Thr Thr Leu Tyr Arg Ile Leu Gln Arg Arg Phe Leu Ala Val Gln
                275                 280                 285

Ser Val Ile Ser Gly Arg Phe Arg Cys Pro Thr Lys Cys Glu Val Glu
                290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
                340                 345                 350

Gly Glu Pro Pro Ser Cys Ala Glu Gly Gln Ser Cys Ala Ser Glu Arg
                355                 360                 365

Gln Gln Ala Leu Ser Arg Leu Tyr Phe Gly Thr Ser Gly Tyr Phe Ser
                370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
                420                 425                 430

Phe Ser Val Ser Glu Asn Leu Leu Lys Glu Ala Ile Arg Ala Ile Phe
                435                 440                 445

Pro Ser Arg Gly Leu Ala Arg Leu Ala Leu Gln Phe Thr Thr Asn Pro
                450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495
```

-continued

```
Phe Ser Gln Phe Phe Gln Gln Leu Gly Leu Ala Ser Phe Leu Asn Gly
            500                 505                 510
Gly Arg Gln Glu Asp Leu Ala Lys Pro Leu Ser Val Gly Leu Asp Ser
            515                 520                 525
Asn Ser Ser Thr Gly Thr Pro Glu Ala Ala Lys Lys Asp Gly Thr Met
            530                 535                 540
Asn Lys Pro Thr Val Gly Ser Phe Gly Phe Glu Ile Asn Leu Gln Glu
545                 550                 555                 560
Asn Gln Asn Ala Leu Lys Phe Leu Ala Ser Leu Leu Glu Leu Pro Glu
                565                 570                 575
Phe Leu Leu Phe Leu Gln His Ala Ile Ser Val Pro Glu Asp Val Ala
            580                 585                 590
Arg Asp Leu Gly Asp Val Met Glu Thr Val Leu Ser Ser Gln Thr Cys
            595                 600                 605
Glu Gln Thr Pro Glu Arg Leu Phe Val Pro Ser Cys Thr Thr Glu Gly
            610                 615                 620
Ser Tyr Glu Asp Val Gln Cys Phe Ser Gly Glu Cys Trp Cys Val Asn
625                 630                 635                 640
Ser Trp Gly Lys Glu Leu Pro Gly Ser Arg Val Arg Gly Gly Gln Pro
                645                 650                 655
Arg Cys Pro Thr Asp Cys Glu Lys Gln Arg Ala Arg Met Gln Ser Leu
            660                 665                 670
Met Gly Ser Gln Pro Ala Gly Ser Thr Leu Phe Val Pro Ala Cys Thr
            675                 680                 685
Ser Glu Gly His Phe Leu Pro Val Gln Cys Phe Asn Ser Glu Cys Tyr
            690                 695                 700
Cys Val Asp Ala Glu Gly Gln Ala Ile Pro Gly Thr Arg Ser Ala Ile
705                 710                 715                 720
Gly Lys Pro Lys Lys Cys Pro Thr Pro Cys Gln Leu Gln Ser Glu Gln
                725                 730                 735
Ala Phe Leu Arg Thr Val Gln Ala Leu Leu Ser Asn Ser Ser Met Leu
            740                 745                 750
Pro Thr Leu Ser Asp Thr Tyr Ile Pro Gln Cys Ser Thr Asp Gly Gln
            755                 760                 765
Trp Arg Gln Val Gln Cys Asn Gly Pro Pro Glu Gln Val Phe Glu Leu
            770                 775                 780
Tyr Gln Arg Trp Glu Ala Gln Asn Lys Gly Gln Asp Leu Thr Pro Ala
785                 790                 795                 800
Lys Leu Leu Val Lys Ile Met Ser Tyr Arg Glu Ala Ala Ser Gly Asn
                805                 810                 815
Phe Ser Leu Phe Ile Gln Ser Leu Tyr Glu Ala Gly Gln Gln Asp Val
            820                 825                 830
Phe Pro Val Leu Ser Gln Tyr Pro Ser Leu Gln Asp Val Pro Leu Ala
            835                 840                 845
Ala Leu Glu Gly Lys Arg Pro Gln Pro Arg Glu Asn Ile Leu Leu Glu
            850                 855                 860
Pro Tyr Leu Phe Trp Gln Ile Leu Asn Gly Gln Leu Ser Gln Tyr Pro
865                 870                 875                 880
Gly Ser Tyr Ser Asp Phe Ser Thr Pro Leu Ala His Phe Asp Leu Arg
                885                 890                 895
Asn Cys Trp Cys Val Asp Glu Ala Gly Gln Glu Leu Glu Gly Met Arg
            900                 905                 910
```

```
Ser Glu Pro Ser Lys Leu Pro Thr Cys Pro Gly Ser Cys Glu Glu Ala
            915                 920                 925

Lys Leu Arg Val Leu Gln Phe Ile Arg Glu Thr Glu Glu Ile Val Ser
    930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
                965                 970                 975

Pro Pro Arg Glu Ala Phe Ala Glu Gln Phe Leu Arg Gly Ser Asp Tyr
            980                 985                 990

Ala Ile Arg Leu Ala Ala Gln Ser Thr Leu Ser Phe Tyr Gln Arg Arg
            995                1000                1005

Arg Phe Ser Pro Asp Asp Ser Ala Gly Ala Ser Ala Leu Leu Arg
    1010                1015                1020

Ser Gly Pro Tyr Met Pro Gln Cys Asp Ala Phe Gly Ser Trp Glu
    1025                1030                1035

Pro Val Gln Cys His Ala Gly Thr Gly His Cys Trp Cys Val Asp
    1040                1045                1050

Glu Lys Gly Gly Phe Ile Pro Gly Ser Leu Thr Ala Arg Ser Leu
    1055                1060                1065

Gln Ile Pro Gln Cys Pro Thr Thr Cys Glu Lys Ser Arg Thr Ser
    1070                1075                1080

Gly Leu Leu Ser Ser Trp Lys Gln Ala Arg Ser Gln Glu Asn Pro
    1085                1090                1095

Ser Pro Lys Asp Leu Phe Val Pro Ala Cys Leu Glu Thr Gly Glu
    1100                1105                1110

Tyr Ala Arg Leu Gln Ala Ser Gly Ala Gly Thr Trp Cys Val Asp
    1115                1120                1125

Pro Ala Ser Gly Glu Glu Leu Arg Pro Gly Ser Ser Ser Ser Ala
    1130                1135                1140

Gln Cys Pro Ser Leu Cys Asn Val Leu Lys Ser Gly Val Leu Ser
    1145                1150                1155

Arg Arg Val Ser Pro Gly Tyr Val Pro Ala Cys Arg Ala Glu Asp
    1160                1165                1170

Gly Gly Phe Ser Pro Val Gln Cys Asp Gln Ala Gln Gly Ser Cys
    1175                1180                1185

Trp Cys Val Met Asp Ser Gly Glu Glu Val Pro Gly Thr Arg Val
    1190                1195                1200

Thr Gly Gly Gln Pro Ala Cys Glu Ser Pro Arg Cys Pro Leu Pro
    1205                1210                1215

Phe Asn Ala Ser Glu Val Val Gly Gly Thr Ile Leu Cys Glu Thr
    1220                1225                1230

Ile Ser Gly Pro Thr Gly Ser Ala Met Gln Gln Cys Gln Leu Leu
    1235                1240                1245

Cys Arg Gln Gly Ser Trp Ser Val Phe Pro Pro Gly Pro Leu Ile
    1250                1255                1260

Cys Ser Leu Glu Ser Gly Arg Trp Glu Ser Gln Leu Pro Gln Pro
    1265                1270                1275

Arg Ala Cys Gln Arg Pro Gln Leu Trp Gln Thr Ile Gln Thr Gln
    1280                1285                1290

Gly His Phe Gln Leu Gln Leu Pro Pro Gly Lys Met Cys Ser Ala
    1295                1300                1305

Asp Tyr Ala Asp Leu Leu Gln Thr Phe Gln Val Phe Ile Leu Asp
```

```
            1310                1315                1320

Glu Leu Thr Ala Arg Gly Phe Cys Gln Ile Gln Val Lys Thr Phe
    1325                1330                1335

Gly Thr Leu Val Ser Ile Pro Val Cys Asn Asn Ser Ser Val Gln
    1340                1345                1350

Val Gly Cys Leu Thr Arg Glu Arg Leu Gly Val Asn Val Thr Trp
    1355                1360                1365

Lys Ser Arg Leu Glu Asp Ile Pro Val Ala Ser Leu Pro Asp Leu
    1370                1375                1380

His Asp Ile Glu Arg Ala Leu Val Gly Lys Asp Leu Leu Gly Arg
    1385                1390                1395

Phe Thr Asp Leu Ile Gln Ser Gly Ser Phe Gln Leu His Leu Asp
    1400                1405                1410

Ser Lys Thr Phe Pro Ala Glu Thr Ile Arg Phe Leu Gln Gly Asp
    1415                1420                1425

His Phe Gly Thr Ser Pro Arg Thr Trp Phe Gly Cys Ser Glu Gly
    1430                1435                1440

Phe Tyr Gln Val Leu Thr Ser Glu Ala Ser Gln Asp Gly Leu Gly
    1445                1450                1455

Cys Val Lys Cys Pro Glu Gly Ser Tyr Ser Gln Asp Glu Glu Cys
    1460                1465                1470

Ile Pro Cys Pro Val Gly Phe Tyr Gln Glu Gln Ala Gly Ser Leu
    1475                1480                1485

Ala Cys Val Pro Cys Pro Val Gly Arg Thr Thr Ile Ser Ala Gly
    1490                1495                1500

Ala Phe Ser Gln Thr His Cys Val Thr Asp Cys Gln Arg Asn Glu
    1505                1510                1515

Ala Gly Leu Gln Cys Asp Gln Asn Gly Gln Tyr Arg Ala Ser Gln
    1520                1525                1530

Lys Asp Arg Gly Ser Gly Lys Ala Phe Cys Val Asp Gly Glu Gly
    1535                1540                1545

Arg Arg Leu Pro Trp Trp Glu Thr Glu Ala Pro Leu Glu Asp Ser
    1550                1555                1560

Gln Cys Leu Met Met Gln Lys Phe Glu Lys Val Pro Glu Ser Lys
    1565                1570                1575

Val Ile Phe Asp Ala Asn Ala Pro Val Ala Val Arg Ser Lys Val
    1580                1585                1590

Pro Asp Ser Glu Phe Pro Val Met Gln Cys Leu Thr Asp Cys Thr
    1595                1600                1605

Glu Asp Glu Ala Cys Ser Phe Phe Thr Val Ser Thr Thr Glu Pro
    1610                1615                1620

Glu Ile Ser Cys Asp Phe Tyr Ala Trp Thr Ser Asp Asn Val Ala
    1625                1630                1635

Cys Met Thr Ser Asp Gln Lys Arg Asp Ala Leu Gly Asn Ser Lys
    1640                1645                1650

Ala Thr Ser Phe Gly Ser Leu Arg Cys Gln Val Lys Val Arg Ser
    1655                1660                1665

His Gly Gln Asp Ser Pro Ala Val Tyr Leu Lys Lys Gly Gln Gly
    1670                1675                1680

Ser Thr Thr Thr Leu Gln Lys Arg Phe Glu Pro Thr Gly Phe Gln
    1685                1690                1695

Asn Met Leu Ser Gly Leu Tyr Asn Pro Ile Val Phe Ser Ala Ser
    1700                1705                1710
```

-continued

```
Gly Ala Asn Leu Thr Asp Ala His Leu Phe Cys Leu Leu Ala Cys
    1715                1720                1725

Asp Arg Asp Leu Cys Cys Asp Gly Phe Val Leu Thr Gln Val Gln
    1730                1735                1740

Gly Gly Ala Ile Ile Cys Gly Leu Leu Ser Ser Pro Ser Val Leu
    1745                1750                1755

Leu Cys Asn Val Lys Asp Trp Met Asp Pro Ser Glu Ala Trp Ala
    1760                1765                1770

Asn Ala Thr Cys Pro Gly Val Thr Tyr Asp Gln Glu Ser His Gln
    1775                1780                1785

Val Ile Leu Arg Leu Gly Asp Gln Glu Phe Ile Lys Ser Leu Thr
    1790                1795                1800

Pro Leu Glu Gly Thr Gln Asp Thr Phe Thr Asn Phe Gln Gln Val
    1805                1810                1815

Tyr Leu Trp Lys Asp Ser Asp Met Gly Ser Arg Pro Glu Ser Met
    1820                1825                1830

Gly Cys Arg Lys Asp Thr Val Pro Arg Pro Ala Ser Pro Thr Glu
    1835                1840                1845

Ala Gly Leu Thr Thr Glu Leu Phe Ser Pro Val Asp Leu Asn Gln
    1850                1855                1860

Val Ile Val Asn Gly Asn Gln Ser Leu Ser Ser Gln Lys His Trp
    1865                1870                1875

Leu Phe Lys His Leu Phe Ser Ala Gln Gln Ala Asn Leu Trp Cys
    1880                1885                1890

Leu Ser Arg Cys Val Gln Glu His Ser Phe Cys Gln Leu Ala Glu
    1895                1900                1905

Ile Thr Glu Ser Ala Ser Leu Tyr Phe Thr Cys Thr Leu Tyr Pro
    1910                1915                1920

Glu Ala Gln Val Cys Asp Asp Ile Met Glu Ser Asn Ala Gln Gly
    1925                1930                1935

Cys Arg Leu Ile Leu Pro Gln Met Pro Lys Ala Leu Phe Arg Lys
    1940                1945                1950

Lys Val Ile Leu Glu Asp Lys Val Lys Asn Phe Tyr Thr Arg Leu
    1955                1960                1965

Pro Phe Gln Lys Leu Met Gly Ile Ser Ile Arg Asn Lys Val Pro
    1970                1975                1980

Met Ser Glu Lys Ser Ile Ser Asn Gly Phe Phe Glu Cys Glu Arg
    1985                1990                1995

Arg Cys Asp Ala Asp Pro Cys Cys Thr Gly Phe Gly Phe Leu Asn
    2000                2005                2010

Val Ser Gln Leu Lys Gly Gly Glu Val Thr Cys Leu Thr Leu Asn
    2015                2020                2025

Ser Leu Gly Ile Gln Met Cys Ser Glu Glu Asn Gly Gly Ala Trp
    2030                2035                2040

Arg Ile Leu Asp Cys Gly Ser Pro Asp Ile Glu Val His Thr Tyr
    2045                2050                2055

Pro Phe Gly Trp Tyr Gln Lys Pro Ile Ala Gln Asn Asn Ala Pro
    2060                2065                2070

Ser Phe Cys Pro Leu Val Val Leu Pro Ser Leu Thr Glu Lys Val
    2075                2080                2085

Ser Leu Asp Ser Trp Gln Ser Leu Ala Leu Ser Ser Val Val Val
    2090                2095                2100
```

-continued

```
Asp Pro Ser Ile Arg His Phe Asp Val Ala His Val Ser Thr Ala
    2105                2110                2115
Ala Thr Ser Asn Phe Ser Ala Val Arg Asp Leu Cys Leu Ser Glu
    2120                2125                2130
Cys Ser Gln His Glu Ala Cys Leu Ile Thr Thr Leu Gln Thr Gln
    2135                2140                2145
Pro Gly Ala Val Arg Cys Met Phe Tyr Ala Asp Thr Gln Ser Cys
    2150                2155                2160
Thr His Ser Leu Gln Gly Gln Asn Cys Arg Leu Leu Leu Arg Glu
    2165                2170                2175
Glu Ala Thr His Ile Tyr Arg Lys Pro Gly Ile Ser Leu Leu Ser
    2180                2185                2190
Tyr Glu Ala Ser Val Pro Ser Val Pro Ile Ser Thr His Gly Arg
    2195                2200                2205
Leu Leu Gly Arg Ser Gln Ala Ile Gln Val Gly Thr Ser Trp Lys
    2210                2215                2220
Gln Val Asp Gln Phe Leu Gly Val Pro Tyr Ala Ala Pro Pro Leu
    2225                2230                2235
Ala Glu Arg Arg Phe Gln Ala Pro Glu Pro Leu Asn Trp Thr Gly
    2240                2245                2250
Ser Trp Asp Ala Ser Lys Pro Arg Ala Ser Cys Trp Gln Pro Gly
    2255                2260                2265
Thr Arg Thr Ser Thr Ser Pro Gly Val Ser Glu Asp Cys Leu Tyr
    2270                2275                2280
Leu Asn Val Phe Ile Pro Gln Asn Val Ala Pro Asn Ala Ser Val
    2285                2290                2295
Leu Val Phe Phe His Asn Thr Met Asp Arg Glu Glu Ser Glu Gly
    2300                2305                2310
Trp Pro Ala Ile Asp Gly Ser Phe Leu Ala Ala Val Gly Asn Leu
    2315                2320                2325
Ile Val Val Thr Ala Ser Tyr Arg Val Gly Val Phe Gly Phe Leu
    2330                2335                2340
Ser Ser Gly Ser Gly Glu Val Ser Gly Asn Trp Gly Leu Leu Asp
    2345                2350                2355
Gln Val Ala Ala Leu Thr Trp Val Gln Thr His Ile Arg Gly Phe
    2360                2365                2370
Gly Gly Asp Pro Arg Arg Val Ser Leu Ala Ala Asp Arg Gly Gly
    2375                2380                2385
Ala Asp Val Ala Ser Ile His Leu Leu Thr Ala Arg Ala Thr Asn
    2390                2395                2400
Ser Gln Leu Phe Arg Arg Ala Val Leu Met Gly Gly Ser Ala Leu
    2405                2410                2415
Ser Pro Ala Ala Val Ile Ser His Glu Arg Ala Gln Gln Gln Ala
    2420                2425                2430
Ile Ala Leu Ala Lys Glu Val Ser Cys Pro Met Ser Ser Ser Gln
    2435                2440                2445
Glu Val Val Ser Cys Leu Arg Gln Lys Pro Ala Asn Val Leu Asn
    2450                2455                2460
Asp Ala Gln Thr Lys Leu Leu Ala Val Ser Gly Pro Phe His Tyr
    2465                2470                2475
Trp Gly Pro Val Ile Asp Gly His Phe Leu Arg Glu Pro Pro Ala
    2480                2485                2490
Arg Ala Leu Lys Arg Ser Leu Trp Val Glu Val Asp Leu Leu Ile
```

```
                 2495                2500                2505

Gly Ser Ser Gln Asp Asp Gly Leu Ile Asn Arg Ala Lys Ala Val
         2510                2515                2520

Lys Gln Phe Glu Glu Ser Arg Gly Arg Thr Ser Ser Lys Thr Ala
         2525                2530                2535

Phe Tyr Gln Ala Leu Gln Asn Ser Leu Gly Gly Glu Asp Ser Asp
         2540                2545                2550

Ala Arg Val Glu Ala Ala Thr Trp Tyr Tyr Ser Leu Glu His
         2555                2560                2565

Ser Thr Asp Asp Tyr Ala Ser Phe Ser Arg Ala Leu Glu Asn Ala
         2570                2575                2580

Thr Arg Asp Tyr Phe Ile Ile Cys Pro Ile Ile Asp Met Ala Ser
         2585                2590                2595

Ala Trp Ala Lys Arg Ala Arg Gly Asn Val Phe Met Tyr His Ala
         2600                2605                2610

Pro Glu Asn Tyr Gly His Gly Ser Leu Glu Leu Leu Ala Asp Val
         2615                2620                2625

Gln Phe Ala Leu Gly Leu Pro Phe Tyr Pro Ala Tyr Glu Gly Gln
         2630                2635                2640

Phe Ser Leu Glu Glu Lys Ser Leu Ser Leu Lys Ile Met Gln Tyr
         2645                2650                2655

Phe Ser His Phe Ile Arg Ser Gly Asn Pro Asn Tyr Pro Tyr Glu
         2660                2665                2670

Phe Ser Arg Lys Val Pro Thr Phe Ala Thr Pro Trp Pro Asp Phe
         2675                2680                2685

Val Pro Arg Ala Gly Gly Glu Asn Tyr Lys Glu Phe Ser Glu Leu
         2690                2695                2700

Leu Pro Asn Arg Gln Gly Leu Lys Lys Ala Asp Cys Ser Phe Trp
         2705                2710                2715

Ser Lys Tyr Ile Ser Ser Leu Lys Thr Ser Ala Asp Gly Ala Lys
         2720                2725                2730

Gly Gly Gln Ser Ala Glu Ser Glu Glu Glu Leu Thr Ala Gly
         2735                2740                2745

Ser Gly Leu Arg Glu Asp Leu Leu Ser Leu Gln Glu Pro Gly Ser
         2750                2755                2760

Lys Thr Tyr Ser Lys
         2765

<210> SEQ ID NO 4
<211> LENGTH: 2711
<212> TYPE: PRT
<213> ORGANISM: Homo sapiens

<400> SEQUENCE: 4

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
                20                  25                  30

Pro Cys Glu Leu Gln Arg Glu Thr Ala Phe Leu Lys Gln Ala Asp Tyr
            35                  40                  45

Val Pro Gln Cys Ala Glu Asp Gly Ser Phe Gln Thr Val Gln Cys Gln
        50                  55                  60

Asn Asp Gly Arg Ser Cys Trp Cys Val Gly Ala Asn Gly Ser Glu Val
65                  70                  75                  80
```

-continued

```
Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
            115                 120                 125

Val Gln Cys Asp Val Gln Gln Val Gln Cys Trp Cys Val Asp Ala Glu
130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
            195                 200                 205

His Ser Tyr Asn Arg Phe Pro Asp Ala Phe Val Thr Phe Ser Ser Phe
        210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270

Glu Thr Thr Leu Tyr Arg Ile Leu Gln Arg Arg Phe Leu Ala Val Gln
            275                 280                 285

Ser Val Ile Ser Gly Arg Phe Arg Cys Pro Thr Lys Cys Glu Val Glu
290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
            340                 345                 350

Gly Glu Pro Pro Ser Cys Ala Glu Gly Gln Ser Cys Ala Ser Glu Arg
            355                 360                 365

Gln Gln Ala Leu Ser Arg Leu Tyr Phe Gly Thr Ser Gly Tyr Phe Ser
            370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
            435                 440                 445

Pro Ser Arg Gly Leu Ala Arg Leu Ala Leu Gln Phe Thr Thr Asn Pro
            450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Phe Gln Gln Leu Gly Leu Ala Ser Phe Leu Asn Gly
```

```
                500             505             510
Gly Arg Gln Glu Asp Leu Ala Lys Pro Leu Ser Val Gly Leu Asp Ser
            515                 520             525

Asn Ser Ser Thr Gly Thr Pro Glu Ala Ala Lys Lys Asp Gly Thr Met
        530                 535             540

Asn Lys Pro Thr Val Gly Ser Phe Gly Phe Glu Ile Asn Leu Gln Glu
545                 550             555                 560

Asn Gln Asn Ala Leu Lys Phe Leu Ala Ser Leu Leu Glu Leu Pro Glu
                565             570             575

Phe Leu Leu Phe Leu Gln His Ala Ile Ser Val Pro Glu Asp Val Ala
            580             585             590

Arg Asp Leu Gly Asp Val Met Glu Thr Val Leu Ser Ser Gln Thr Cys
        595                 600             605

Glu Gln Thr Pro Glu Arg Leu Phe Val Pro Ser Cys Thr Thr Glu Gly
    610                 615             620

Ser Tyr Glu Asp Val Gln Cys Phe Ser Gly Glu Cys Trp Cys Val Asn
625                 630             635                 640

Ser Trp Gly Lys Glu Leu Pro Gly Ser Arg Val Arg Gly Gly Gln Pro
                645             650             655

Arg Cys Pro Thr Asp Cys Glu Lys Gln Arg Ala Arg Met Gln Ser Leu
            660             665             670

Met Gly Ser Gln Pro Ala Gly Ser Thr Leu Phe Val Pro Ala Cys Thr
        675             680             685

Ser Glu Gly His Phe Leu Pro Val Gln Cys Phe Asn Ser Glu Cys Tyr
    690             695             700

Cys Val Asp Ala Glu Gly Gln Ala Ile Pro Gly Thr Arg Ser Ala Ile
705             710             715                 720

Gly Lys Pro Lys Lys Cys Pro Thr Pro Cys Gln Leu Gln Ser Glu Gln
                725             730             735

Ala Phe Leu Arg Thr Val Gln Ala Leu Leu Ser Asn Ser Ser Met Leu
            740             745             750

Pro Thr Leu Ser Asp Thr Tyr Ile Pro Gln Cys Ser Thr Asp Gly Gln
        755             760             765

Trp Arg Gln Val Gln Cys Asn Gly Pro Pro Glu Gln Val Phe Glu Leu
    770             775             780

Tyr Gln Arg Trp Glu Ala Gln Asn Lys Gly Gln Asp Leu Thr Pro Ala
785             790             795                 800

Lys Leu Leu Val Lys Ile Met Ser Tyr Arg Glu Ala Ala Ser Gly Asn
                805             810             815

Phe Ser Leu Phe Ile Gln Ser Leu Tyr Glu Ala Gly Gln Gln Asp Val
            820             825             830

Phe Pro Val Leu Ser Gln Tyr Pro Ser Leu Gln Asp Val Pro Leu Ala
        835             840             845

Ala Leu Glu Gly Lys Arg Pro Gln Pro Arg Glu Asn Ile Leu Leu Glu
    850             855             860

Pro Tyr Leu Phe Trp Gln Ile Leu Asn Gly Gln Leu Ser Gln Tyr Pro
865             870             875                 880

Gly Ser Tyr Ser Asp Phe Ser Thr Pro Leu Ala His Phe Asp Leu Arg
                885             890             895

Asn Cys Trp Cys Val Asp Glu Ala Gly Gln Glu Leu Glu Gly Met Arg
            900             905             910

Ser Glu Pro Ser Lys Leu Pro Thr Cys Pro Gly Ser Cys Glu Glu Ala
        915             920             925
```

```
Lys Leu Arg Val Leu Gln Phe Ile Arg Glu Thr Glu Glu Ile Val Ser
    930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
            965                 970                 975

Pro Pro Arg Glu Ala Phe Ala Glu Gln Phe Leu Arg Gly Ser Asp Tyr
        980                 985                 990

Ala Ile Arg Leu Ala Ala Gln Ser Thr Leu Ser Phe Tyr Gln Arg Arg
        995                 1000                1005

Arg Phe Ser Pro Asp Asp Ser Ala Gly Ala Ser Ala Leu Leu Arg
    1010                1015                1020

Ser Gly Pro Tyr Met Pro Gln Cys Asp Ala Phe Gly Ser Trp Glu
    1025                1030                1035

Pro Val Gln Cys His Ala Gly Thr Gly His Cys Trp Cys Val Asp
    1040                1045                1050

Glu Lys Gly Gly Phe Ile Pro Gly Ser Leu Thr Ala Arg Ser Leu
    1055                1060                1065

Gln Ile Pro Gln Cys Pro Thr Thr Cys Glu Lys Ser Arg Thr Ser
    1070                1075                1080

Gly Leu Leu Ser Ser Trp Lys Gln Ala Arg Ser Gln Glu Asn Pro
    1085                1090                1095

Ser Pro Lys Asp Leu Phe Val Pro Ala Cys Leu Glu Thr Gly Glu
    1100                1105                1110

Tyr Ala Arg Leu Gln Ala Ser Gly Ala Gly Thr Trp Cys Val Asp
    1115                1120                1125

Pro Ala Ser Gly Glu Glu Leu Arg Pro Gly Ser Ser Ser Ser Ala
    1130                1135                1140

Gln Cys Pro Ser Leu Cys Asn Val Leu Lys Ser Gly Val Leu Ser
    1145                1150                1155

Arg Arg Val Ser Pro Gly Tyr Val Pro Ala Cys Arg Ala Glu Asp
    1160                1165                1170

Gly Gly Phe Ser Pro Val Gln Cys Asp Gln Ala Gln Gly Ser Cys
    1175                1180                1185

Trp Cys Val Met Asp Ser Gly Glu Glu Val Pro Gly Thr Arg Val
    1190                1195                1200

Thr Gly Gly Gln Pro Ala Cys Glu Ser Pro Arg Cys Pro Leu Pro
    1205                1210                1215

Phe Asn Ala Ser Glu Val Val Gly Gly Thr Ile Leu Cys Glu Thr
    1220                1225                1230

Ile Ser Gly Pro Thr Gly Ser Ala Met Gln Gln Cys Gln Leu Leu
    1235                1240                1245

Cys Arg Gln Gly Ser Trp Ser Val Phe Pro Pro Gly Pro Leu Ile
    1250                1255                1260

Cys Ser Leu Glu Ser Gly Arg Trp Glu Ser Gln Leu Pro Gln Pro
    1265                1270                1275

Arg Ala Cys Gln Arg Pro Gln Leu Trp Gln Thr Ile Gln Thr Gln
    1280                1285                1290

Gly His Phe Gln Leu Gln Leu Pro Pro Gly Lys Met Cys Ser Ala
    1295                1300                1305

Asp Tyr Ala Asp Leu Leu Gln Thr Phe Gln Val Phe Ile Leu Asp
    1310                1315                1320
```

| | | | | | | | | | | | |
|---|---|---|---|---|---|---|---|---|---|---|---|
| Glu | Leu | Thr | Ala | Arg | Gly | Phe | Cys | Gln | Ile | Gln | Val | Lys | Thr | Phe |
| 1325 | | | | | 1330 | | | | | 1335 | | | | |
| Gly | Thr | Leu | Val | Ser | Ile | Pro | Val | Cys | Asn | Asn | Ser | Ser | Val | Gln |
| 1340 | | | | | 1345 | | | | | 1350 | | | | |
| Val | Gly | Cys | Leu | Thr | Arg | Glu | Arg | Leu | Gly | Val | Asn | Val | Thr | Trp |
| 1355 | | | | | 1360 | | | | | 1365 | | | | |
| Lys | Ser | Arg | Leu | Glu | Asp | Ile | Pro | Val | Ala | Ser | Leu | Pro | Asp | Leu |
| 1370 | | | | | 1375 | | | | | 1380 | | | | |
| His | Asp | Ile | Glu | Arg | Ala | Leu | Val | Gly | Lys | Asp | Leu | Leu | Gly | Arg |
| 1385 | | | | | 1390 | | | | | 1395 | | | | |
| Phe | Thr | Asp | Leu | Ile | Gln | Ser | Gly | Ser | Phe | Gln | Leu | His | Leu | Asp |
| 1400 | | | | | 1405 | | | | | 1410 | | | | |
| Ser | Lys | Thr | Phe | Pro | Ala | Glu | Thr | Ile | Arg | Phe | Leu | Gln | Gly | Asp |
| 1415 | | | | | 1420 | | | | | 1425 | | | | |
| His | Phe | Gly | Thr | Ser | Pro | Arg | Thr | Trp | Phe | Gly | Cys | Ser | Glu | Gly |
| 1430 | | | | | 1435 | | | | | 1440 | | | | |
| Phe | Tyr | Gln | Val | Leu | Thr | Ser | Glu | Ala | Ser | Gln | Asp | Gly | Leu | Gly |
| 1445 | | | | | 1450 | | | | | 1455 | | | | |
| Cys | Val | Lys | Cys | Pro | Glu | Gly | Ser | Tyr | Ser | Gln | Asp | Glu | Glu | Cys |
| 1460 | | | | | 1465 | | | | | 1470 | | | | |
| Ile | Pro | Cys | Pro | Val | Gly | Phe | Tyr | Gln | Glu | Gln | Ala | Gly | Ser | Leu |
| 1475 | | | | | 1480 | | | | | 1485 | | | | |
| Ala | Cys | Val | Pro | Cys | Pro | Val | Gly | Arg | Thr | Thr | Ile | Ser | Ala | Gly |
| 1490 | | | | | 1495 | | | | | 1500 | | | | |
| Ala | Phe | Ser | Gln | Thr | His | Leu | Met | Gln | Lys | Phe | Glu | Lys | Val | Pro |
| 1505 | | | | | 1510 | | | | | 1515 | | | | |
| Glu | Ser | Lys | Val | Ile | Phe | Asp | Ala | Asn | Ala | Pro | Val | Ala | Val | Arg |
| 1520 | | | | | 1525 | | | | | 1530 | | | | |
| Ser | Lys | Val | Pro | Asp | Ser | Glu | Phe | Pro | Val | Met | Gln | Cys | Leu | Thr |
| 1535 | | | | | 1540 | | | | | 1545 | | | | |
| Asp | Cys | Thr | Glu | Asp | Glu | Ala | Cys | Ser | Phe | Phe | Thr | Val | Ser | Thr |
| 1550 | | | | | 1555 | | | | | 1560 | | | | |
| Thr | Glu | Pro | Glu | Ile | Ser | Cys | Asp | Phe | Tyr | Ala | Trp | Thr | Ser | Asp |
| 1565 | | | | | 1570 | | | | | 1575 | | | | |
| Asn | Val | Ala | Cys | Met | Thr | Ser | Asp | Gln | Lys | Arg | Asp | Ala | Leu | Gly |
| 1580 | | | | | 1585 | | | | | 1590 | | | | |
| Asn | Ser | Lys | Ala | Thr | Ser | Phe | Gly | Ser | Leu | Arg | Cys | Gln | Val | Lys |
| 1595 | | | | | 1600 | | | | | 1605 | | | | |
| Val | Arg | Ser | His | Gly | Gln | Asp | Ser | Pro | Ala | Val | Tyr | Leu | Lys | Lys |
| 1610 | | | | | 1615 | | | | | 1620 | | | | |
| Gly | Gln | Gly | Ser | Thr | Thr | Thr | Leu | Gln | Lys | Arg | Phe | Glu | Pro | Thr |
| 1625 | | | | | 1630 | | | | | 1635 | | | | |
| Gly | Phe | Gln | Asn | Met | Leu | Ser | Gly | Leu | Tyr | Asn | Pro | Ile | Val | Phe |
| 1640 | | | | | 1645 | | | | | 1650 | | | | |
| Ser | Ala | Ser | Gly | Ala | Asn | Leu | Thr | Asp | Ala | His | Leu | Phe | Cys | Leu |
| 1655 | | | | | 1660 | | | | | 1665 | | | | |
| Leu | Ala | Cys | Asp | Arg | Asp | Leu | Cys | Cys | Asp | Gly | Phe | Val | Leu | Thr |
| 1670 | | | | | 1675 | | | | | 1680 | | | | |
| Gln | Val | Gln | Gly | Gly | Ala | Ile | Ile | Cys | Gly | Leu | Leu | Ser | Ser | Pro |
| 1685 | | | | | 1690 | | | | | 1695 | | | | |
| Ser | Val | Leu | Leu | Cys | Asn | Val | Lys | Asp | Trp | Met | Asp | Pro | Ser | Glu |
| 1700 | | | | | 1705 | | | | | 1710 | | | | |
| Ala | Trp | Ala | Asn | Ala | Thr | Cys | Pro | Gly | Val | Thr | Tyr | Asp | Gln | Glu |

```
                 1715                1720                1725

Ser His Gln Val Ile Leu Arg Leu Gly Asp Gln Glu Phe Ile Lys
    1730                1735                1740

Ser Leu Thr Pro Leu Glu Gly Thr Gln Asp Thr Phe Thr Asn Phe
    1745                1750                1755

Gln Gln Val Tyr Leu Trp Lys Asp Ser Asp Met Gly Ser Arg Pro
    1760                1765                1770

Glu Ser Met Gly Cys Arg Lys Asp Thr Val Pro Arg Pro Ala Ser
    1775                1780                1785

Pro Thr Glu Ala Gly Leu Thr Thr Glu Leu Phe Ser Pro Val Asp
    1790                1795                1800

Leu Asn Gln Val Ile Val Asn Gly Asn Gln Ser Leu Ser Ser Gln
    1805                1810                1815

Lys His Trp Leu Phe Lys His Leu Phe Ser Ala Gln Gln Ala Asn
    1820                1825                1830

Leu Trp Cys Leu Ser Arg Cys Val Gln Glu His Ser Phe Cys Gln
    1835                1840                1845

Leu Ala Glu Ile Thr Glu Ser Ala Ser Leu Tyr Phe Thr Cys Thr
    1850                1855                1860

Leu Tyr Pro Glu Ala Gln Val Cys Asp Asp Ile Met Glu Ser Asn
    1865                1870                1875

Ala Gln Gly Cys Arg Leu Ile Leu Pro Gln Met Pro Lys Ala Leu
    1880                1885                1890

Phe Arg Lys Lys Val Ile Leu Glu Asp Lys Val Lys Asn Phe Tyr
    1895                1900                1905

Thr Arg Leu Pro Phe Gln Lys Leu Met Gly Ile Ser Ile Arg Asn
    1910                1915                1920

Lys Val Pro Met Ser Glu Lys Ser Ile Ser Asn Gly Phe Phe Glu
    1925                1930                1935

Cys Glu Arg Arg Cys Asp Ala Asp Pro Cys Cys Thr Gly Phe Gly
    1940                1945                1950

Phe Leu Asn Val Ser Gln Leu Lys Gly Gly Glu Val Thr Cys Leu
    1955                1960                1965

Thr Leu Asn Ser Leu Gly Ile Gln Met Cys Ser Glu Glu Asn Gly
    1970                1975                1980

Gly Ala Trp Arg Ile Leu Asp Cys Gly Ser Pro Asp Ile Glu Val
    1985                1990                1995

His Thr Tyr Pro Phe Gly Trp Tyr Gln Lys Pro Ile Ala Gln Asn
    2000                2005                2010

Asn Ala Pro Ser Phe Cys Pro Leu Val Val Leu Pro Ser Leu Thr
    2015                2020                2025

Glu Lys Val Ser Leu Asp Ser Trp Gln Ser Leu Ala Leu Ser Ser
    2030                2035                2040

Val Val Val Asp Pro Ser Ile Arg His Phe Asp Val Ala His Val
    2045                2050                2055

Ser Thr Ala Ala Thr Ser Asn Phe Ser Ala Val Arg Asp Leu Cys
    2060                2065                2070

Leu Ser Glu Cys Ser Gln His Glu Ala Cys Leu Ile Thr Thr Leu
    2075                2080                2085

Gln Thr Gln Pro Gly Ala Val Arg Cys Met Phe Tyr Ala Asp Thr
    2090                2095                2100

Gln Ser Cys Thr His Ser Leu Gln Gly Gln Asn Cys Arg Leu Leu
    2105                2110                2115
```

-continued

```
Leu Arg Glu Glu Ala Thr His Ile Tyr Arg Lys Pro Gly Ile Ser
    2120                2125                2130

Leu Leu Ser Tyr Glu Ala Ser Val Pro Ser Val Pro Ile Ser Thr
    2135                2140                2145

His Gly Arg Leu Leu Gly Arg Ser Gln Ala Ile Gln Val Gly Thr
    2150                2155                2160

Ser Trp Lys Gln Val Asp Gln Phe Leu Gly Val Pro Tyr Ala Ala
    2165                2170                2175

Pro Pro Leu Ala Glu Arg Arg Phe Gln Ala Pro Glu Pro Leu Asn
    2180                2185                2190

Trp Thr Gly Ser Trp Asp Ala Ser Lys Pro Arg Ala Ser Cys Trp
    2195                2200                2205

Gln Pro Gly Thr Arg Thr Ser Thr Ser Pro Gly Val Ser Glu Asp
    2210                2215                2220

Cys Leu Tyr Leu Asn Val Phe Ile Pro Gln Asn Val Ala Pro Asn
    2225                2230                2235

Ala Ser Val Leu Val Phe Phe His Asn Thr Met Asp Arg Glu Glu
    2240                2245                2250

Ser Glu Gly Trp Pro Ala Ile Asp Gly Ser Phe Leu Ala Ala Val
    2255                2260                2265

Gly Asn Leu Ile Val Val Thr Ala Ser Tyr Arg Val Gly Val Phe
    2270                2275                2280

Gly Phe Leu Ser Ser Gly Ser Gly Glu Val Ser Gly Asn Trp Gly
    2285                2290                2295

Leu Leu Asp Gln Val Ala Ala Leu Thr Trp Val Gln Thr His Ile
    2300                2305                2310

Arg Gly Phe Gly Gly Asp Pro Arg Arg Val Ser Leu Ala Ala Asp
    2315                2320                2325

Arg Gly Gly Ala Asp Val Ala Ser Ile His Leu Leu Thr Ala Arg
    2330                2335                2340

Ala Thr Asn Ser Gln Leu Phe Arg Arg Ala Val Leu Met Gly Gly
    2345                2350                2355

Ser Ala Leu Ser Pro Ala Ala Val Ile Ser His Glu Arg Ala Gln
    2360                2365                2370

Gln Gln Ala Ile Ala Leu Ala Lys Glu Val Ser Cys Pro Met Ser
    2375                2380                2385

Ser Ser Gln Glu Val Val Ser Cys Leu Arg Gln Lys Pro Ala Asn
    2390                2395                2400

Val Leu Asn Asp Ala Gln Thr Lys Leu Leu Ala Val Ser Gly Pro
    2405                2410                2415

Phe His Tyr Trp Gly Pro Val Ile Asp Gly His Phe Leu Arg Glu
    2420                2425                2430

Pro Pro Ala Arg Ala Leu Lys Arg Ser Leu Trp Val Glu Val Asp
    2435                2440                2445

Leu Leu Ile Gly Ser Ser Gln Asp Asp Gly Leu Ile Asn Arg Ala
    2450                2455                2460

Lys Ala Val Lys Gln Phe Glu Glu Ser Arg Gly Arg Thr Ser Ser
    2465                2470                2475

Lys Thr Ala Phe Tyr Gln Ala Leu Gln Asn Ser Leu Gly Gly Glu
    2480                2485                2490

Asp Ser Asp Ala Arg Val Glu Ala Ala Thr Trp Tyr Tyr Ser
    2495                2500                2505
```

-continued

```
Leu Glu His Ser Thr Asp Asp Tyr Ala Ser Phe Ser Arg Ala Leu
2510                2515                2520

Glu Asn Ala Thr Arg Asp Tyr Phe Ile Ile Cys Pro Ile Ile Asp
    2525                2530                2535

Met Ala Ser Ala Trp Ala Lys Arg Ala Arg Gly Asn Val Phe Met
2540                2545                2550

Tyr His Ala Pro Glu Asn Tyr Gly His Gly Ser Leu Glu Leu Leu
    2555                2560                2565

Ala Asp Val Gln Phe Ala Leu Gly Leu Pro Phe Tyr Pro Ala Tyr
2570                2575                2580

Glu Gly Gln Phe Ser Leu Glu Lys Ser Leu Ser Leu Lys Ile
    2585                2590                2595

Met Gln Tyr Phe Ser His Phe Ile Arg Ser Gly Asn Pro Asn Tyr
2600                2605                2610

Pro Tyr Glu Phe Ser Arg Lys Val Pro Thr Phe Ala Thr Pro Trp
    2615                2620                2625

Pro Asp Phe Val Pro Arg Ala Gly Gly Glu Asn Tyr Lys Glu Phe
2630                2635                2640

Ser Glu Leu Leu Pro Asn Arg Gln Gly Leu Lys Lys Ala Asp Cys
    2645                2650                2655

Ser Phe Trp Ser Lys Tyr Ile Ser Ser Leu Lys Thr Ser Ala Asp
2660                2665                2670

Gly Ala Lys Gly Gly Gln Ser Ala Glu Ser Glu Glu Glu Leu
    2675                2680                2685

Thr Ala Gly Ser Gly Leu Arg Glu Asp Leu Leu Ser Leu Gln Glu
2690                2695                2700

Pro Gly Ser Lys Thr Tyr Ser Lys
    2705                2710

<210> SEQ ID NO 5
<211> LENGTH: 1574
<212> TYPE: PRT
<213> ORGANISM: Homo sapiens

<400> SEQUENCE: 5

Ile Pro Arg Lys Pro Ile Ser Lys Arg Pro Val Arg Pro Ser Leu Pro
1               5                   10                  15

Arg Ser Pro Arg Cys Pro Leu Pro Phe Asn Ala Ser Glu Val Val Gly
                20                  25                  30

Gly Thr Ile Leu Cys Glu Thr Ile Ser Gly Pro Thr Gly Ser Ala Met
            35                  40                  45

Gln Gln Cys Gln Leu Leu Cys Arg Gln Gly Ser Trp Ser Val Phe Pro
        50                  55                  60

Pro Gly Pro Leu Ile Cys Ser Leu Glu Ser Gly Arg Trp Glu Ser Gln
65                  70                  75                  80

Leu Pro Gln Pro Arg Ala Cys Gln Arg Pro Gln Leu Trp Gln Thr Ile
                85                  90                  95

Gln Thr Gln Gly His Phe Gln Leu Gln Leu Pro Pro Gly Lys Met Cys
            100                 105                 110

Ser Ala Asp Tyr Ala Gly Leu Leu Gln Thr Phe Gln Val Phe Ile Leu
        115                 120                 125

Asp Glu Leu Thr Ala Arg Gly Phe Cys Gln Ile Gln Val Lys Thr Phe
    130                 135                 140

Gly Thr Leu Val Ser Ile Pro Val Cys Asn Asn Ser Ser Val Gln Val
145                 150                 155                 160
```

```
Gly Cys Leu Thr Arg Glu Arg Leu Gly Val Asn Val Thr Trp Lys Ser
                165                 170                 175

Arg Leu Glu Asp Ile Pro Val Ala Ser Leu Pro Asp Leu His Asp Ile
            180                 185                 190

Glu Arg Ala Leu Val Gly Lys Asp Leu Leu Gly Arg Phe Thr Asp Leu
        195                 200                 205

Ile Gln Ser Gly Ser Phe Gln Leu His Leu Asp Ser Lys Thr Phe Pro
    210                 215                 220

Ala Glu Thr Ile Arg Phe Leu Gln Gly Asp His Phe Gly Thr Ser Pro
225                 230                 235                 240

Arg Thr Trp Phe Gly Cys Ser Glu Gly Phe Tyr Gln Val Leu Thr Ser
                245                 250                 255

Glu Ala Ser Gln Asp Gly Leu Gly Cys Val Lys Cys Pro Glu Gly Ser
            260                 265                 270

Tyr Ser Gln Asp Glu Glu Cys Ile Pro Cys Pro Val Gly Phe Tyr Gln
        275                 280                 285

Glu Gln Ala Gly Ser Leu Ala Cys Val Pro Cys Pro Val Gly Arg Thr
    290                 295                 300

Thr Ile Ser Ala Gly Ala Phe Ser Gln Thr His Cys Val Thr Asp Cys
305                 310                 315                 320

Gln Arg Asn Glu Ala Gly Leu Gln Cys Asp Gln Asn Gly Gln Tyr Arg
                325                 330                 335

Ala Ser Gln Lys Asp Arg Gly Ser Gly Lys Ala Phe Cys Val Asp Gly
            340                 345                 350

Glu Gly Arg Arg Leu Pro Trp Trp Glu Thr Glu Ala Pro Leu Glu Asp
        355                 360                 365

Ser Gln Cys Leu Met Met Gln Lys Phe Glu Lys Val Pro Glu Ser Lys
    370                 375                 380

Val Ile Phe Asp Ala Asn Ala Pro Val Ala Val Arg Ser Lys Val Pro
385                 390                 395                 400

Asp Ser Glu Phe Pro Val Met Gln Cys Leu Thr Asp Cys Thr Glu Asp
                405                 410                 415

Glu Ala Cys Ser Phe Phe Thr Val Ser Thr Thr Glu Pro Glu Ile Ser
            420                 425                 430

Cys Asp Phe Tyr Ala Trp Thr Ser Asp Asn Val Ala Cys Met Thr Ser
        435                 440                 445

Asp Gln Lys Arg Asp Ala Leu Gly Asn Ser Lys Ala Thr Ser Phe Gly
    450                 455                 460

Ser Leu Arg Cys Gln Val Lys Val Arg Ser His Gly Gln Asp Ser Pro
465                 470                 475                 480

Ala Val Tyr Leu Lys Lys Gly Gln Gly Ser Thr Thr Thr Leu Gln Lys
                485                 490                 495

Arg Phe Glu Pro Thr Gly Phe Gln Asn Met Leu Ser Gly Leu Tyr Asn
            500                 505                 510

Pro Ile Val Phe Ser Ala Ser Gly Ala Asn Leu Thr Asp Ala His Leu
        515                 520                 525

Phe Cys Leu Leu Ala Cys Asp Arg Asp Leu Cys Cys Asp Gly Phe Val
    530                 535                 540

Leu Thr Gln Val Gln Gly Gly Ala Ile Ile Cys Gly Leu Leu Ser Ser
545                 550                 555                 560

Pro Ser Val Leu Leu Cys Asn Val Lys Asp Trp Met Asp Pro Ser Glu
                565                 570                 575
```

```
Ala Trp Ala Asn Ala Thr Cys Pro Gly Val Thr Tyr Asp Gln Glu Ser
            580                 585                 590

His Gln Val Ile Leu Arg Leu Gly Asp Gln Glu Phe Ile Lys Ser Leu
        595                 600                 605

Thr Pro Leu Glu Gly Thr Gln Asp Thr Phe Thr Asn Phe Gln Gln Val
    610                 615                 620

Tyr Leu Trp Lys Asp Ser Asp Met Gly Ser Arg Pro Glu Ser Met Gly
625                 630                 635                 640

Cys Arg Lys Asn Thr Val Pro Arg Pro Ala Ser Pro Thr Glu Ala Gly
                645                 650                 655

Leu Thr Thr Glu Leu Phe Ser Pro Val Asp Leu Asn Gln Val Ile Val
            660                 665                 670

Asn Gly Asn Gln Ser Leu Ser Ser Gln Lys His Trp Leu Phe Lys His
        675                 680                 685

Leu Phe Ser Ala Gln Gln Ala Asn Leu Trp Cys Leu Ser Arg Cys Val
    690                 695                 700

Gln Glu His Ser Phe Cys Gln Leu Ala Glu Ile Thr Glu Ser Ala Ser
705                 710                 715                 720

Leu Tyr Phe Thr Cys Thr Leu Tyr Pro Glu Ala Gln Val Cys Asp Asp
                725                 730                 735

Ile Met Glu Ser Asn Ala Gln Gly Cys Arg Leu Ile Leu Pro Gln Met
            740                 745                 750

Pro Lys Ala Leu Phe Arg Lys Lys Val Ile Leu Glu Asp Lys Val Lys
        755                 760                 765

Asn Phe Tyr Thr Arg Leu Pro Phe Gln Lys Leu Thr Gly Ile Ser Ile
    770                 775                 780

Arg Asn Lys Val Pro Met Ser Glu Lys Ser Ile Ser Asn Gly Phe Phe
785                 790                 795                 800

Glu Cys Glu Arg Arg Cys Asp Ala Asp Pro Cys Cys Thr Gly Phe Gly
                805                 810                 815

Phe Leu Asn Val Ser Gln Leu Lys Gly Gly Glu Val Thr Cys Leu Thr
            820                 825                 830

Leu Asn Ser Leu Gly Ile Gln Met Cys Ser Glu Glu Asn Gly Gly Ala
        835                 840                 845

Trp Arg Ile Leu Asp Cys Gly Ser Pro Asp Ile Glu Val His Thr Tyr
    850                 855                 860

Pro Phe Gly Trp Tyr Gln Lys Pro Ile Ala Gln Asn Asn Ala Pro Ser
865                 870                 875                 880

Phe Cys Pro Leu Val Leu Pro Ser Leu Thr Glu Lys Val Ser Leu
                885                 890                 895

Asp Ser Trp Gln Ser Leu Ala Leu Ser Ser Val Val Asp Pro Ser
            900                 905                 910

Ile Arg His Phe Asp Val Ala His Val Ser Thr Ala Ala Thr Ser Asn
        915                 920                 925

Phe Ser Ala Val Arg Asp Leu Cys Leu Ser Glu Cys Ser Gln His Glu
    930                 935                 940

Ala Cys Leu Ile Thr Thr Leu Gln Thr Gln Pro Gly Ala Val Arg Cys
945                 950                 955                 960

Met Phe Tyr Ala Asp Thr Gln Ser Cys Thr His Ser Leu Gln Gly Gln
                965                 970                 975

Asn Cys Arg Leu Leu Leu Arg Glu Glu Ala Thr His Ile Tyr Arg Lys
            980                 985                 990

Pro Gly Ile Ser Leu Leu Ser Tyr  Glu Ala Ser Val Pro  Ser Val Pro
```

-continued

```
             995                 1000                1005
Ile Ser Thr His Gly Arg Leu Leu Gly Arg Ser Gln Ala Ile Gln
        1010                1015                1020

Val Gly Thr Ser Trp Lys Gln Val Asp Gln Phe Leu Gly Val Pro
        1025                1030                1035

Tyr Ala Ala Pro Pro Leu Ala Glu Arg Arg Phe Gln Ala Pro Glu
        1040                1045                1050

Pro Leu Asn Trp Thr Gly Ser Trp Asp Ala Ser Lys Pro Arg Ala
        1055                1060                1065

Ser Cys Trp Gln Pro Gly Thr Arg Thr Ser Thr Ser Pro Gly Val
        1070                1075                1080

Ser Glu Asp Cys Leu Tyr Leu Asn Val Phe Ile Pro Gln Asn Val
        1085                1090                1095

Ala Pro Asn Ala Ser Val Leu Val Phe Phe His Asn Thr Met Asp
        1100                1105                1110

Arg Glu Glu Ser Glu Gly Trp Pro Ala Ile Asp Gly Ser Phe Leu
        1115                1120                1125

Ala Ala Val Gly Asn Leu Ile Val Val Thr Ala Ser Tyr Arg Val
        1130                1135                1140

Gly Val Phe Gly Phe Leu Ser Ser Gly Ser Gly Glu Val Ser Gly
        1145                1150                1155

Asn Trp Gly Leu Leu Asp Gln Val Ala Ala Leu Thr Trp Val Gln
        1160                1165                1170

Thr His Ile Arg Gly Phe Gly Gly Asp Pro Arg Arg Val Ser Leu
        1175                1180                1185

Ala Ala Asp Arg Gly Gly Ala Asp Val Ala Ser Ile His Leu Leu
        1190                1195                1200

Thr Ala Arg Ala Thr Asn Ser Gln Leu Phe Arg Arg Ala Val Leu
        1205                1210                1215

Met Gly Gly Ser Ala Leu Ser Pro Ala Ala Val Ile Ser His Glu
        1220                1225                1230

Arg Ala Gln Gln Gln Ala Ile Ala Leu Ala Lys Glu Val Ser Cys
        1235                1240                1245

Pro Met Ser Ser Ser Gln Glu Val Val Ser Cys Leu Arg Gln Lys
        1250                1255                1260

Pro Ala Asn Val Leu Asn Asp Ala Gln Thr Lys Leu Leu Ala Val
        1265                1270                1275

Ser Gly Pro Phe His Tyr Trp Gly Pro Val Ile Asp Gly His Phe
        1280                1285                1290

Leu Arg Glu Pro Pro Ala Arg Ala Leu Lys Arg Ser Leu Trp Val
        1295                1300                1305

Glu Val Asp Leu Leu Ile Gly Ser Ser Gln Asp Asp Gly Leu Ile
        1310                1315                1320

Asn Arg Ala Lys Ala Val Lys Gln Phe Glu Glu Ser Gln Gly Arg
        1325                1330                1335

Thr Ser Ser Lys Thr Ala Phe Tyr Gln Ala Leu Gln Asn Ser Leu
        1340                1345                1350

Gly Gly Glu Asp Ser Asp Ala Arg Val Glu Ala Ala Ala Thr Trp
        1355                1360                1365

Tyr Tyr Ser Leu Glu His Ser Thr Asp Asp Tyr Ala Ser Phe Ser
        1370                1375                1380

Arg Ala Leu Glu Asn Ala Thr Arg Asp Tyr Phe Ile Ile Cys Pro
        1385                1390                1395
```

```
Ile Ile Asp Met Ala Ser Ala Trp Ala Lys Arg Ala Arg Gly Asn
    1400            1405                1410

Val Phe Met Tyr His Ala Pro Glu Asn Tyr Gly His Gly Ser Leu
    1415            1420                1425

Glu Leu Leu Ala Asp Val Gln Phe Ala Leu Gly Leu Pro Phe Tyr
    1430            1435                1440

Pro Ala Tyr Glu Gly Gln Phe Ser Leu Glu Glu Lys Ser Leu Ser
    1445            1450                1455

Leu Lys Ile Met Gln Tyr Phe Ser His Phe Ile Arg Ser Gly Asn
    1460            1465                1470

Pro Asn Tyr Pro Tyr Glu Phe Ser Arg Lys Val Pro Thr Phe Ala
    1475            1480                1485

Thr Pro Trp Pro Asp Phe Val Pro Arg Ala Gly Gly Glu Asn Tyr
    1490            1495                1500

Lys Glu Phe Ser Glu Leu Leu Pro Asn Arg Gln Gly Leu Lys Lys
    1505            1510                1515

Ala Asp Cys Ser Phe Trp Ser Lys Tyr Ile Ser Ser Leu Lys Thr
    1520            1525                1530

Ser Ala Asp Gly Ala Lys Gly Gly Gln Ser Ala Glu Ser Glu Glu
    1535            1540                1545

Glu Glu Leu Thr Ala Gly Ser Gly Leu Arg Glu Asp Leu Leu Ser
    1550            1555                1560

Leu Gln Glu Pro Gly Ser Lys Thr Tyr Ser Lys
    1565            1570

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Isotope labeled 13C5 and 15N
<220> FEATURE:
<221> NAME/KEY: MOD_RES
<222> LOCATION: (17)..(17)
<223> OTHER INFORMATION: Isotope labeled 13C5 and 15N

<400> SEQUENCE: 6

Lys Val Pro Glu Ser Lys Val Ile Phe Asp Ala Asn Ala Pro Val Ala
1               5                   10                  15

Val Arg Ser Lys Val Pro Asp Ser
            20

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Pro Glu Ser Lys
1               5

<210> SEQ ID NO 8
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Isotope labeled 13C5 and 15N
<220> FEATURE:
<221> NAME/KEY: MOD_RES
<222> LOCATION: (11)..(11)
<223> OTHER INFORMATION: Isotope labeled 13C5 and 15N

<400> SEQUENCE: 8

Val Ile Phe Asp Ala Asn Ala Pro Val Ala Val Arg
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Pro Asp Ser
1
```

THYROGLOBULIN QUANTITATION BY MASS SPECTROSCOPY

CROSS-REFERENCE TO RELATED APPLICATIONS

This application is a continuation of U.S. application Ser. No. 14/689,542, filed Apr. 17, 2015, which is a continuation of U.S. application Ser. No. 14/031,678, filed Sep. 19, 2013, now U.S. Pat. No. 9,012,394, which claims the benefit under 35 U.S.C. § 119(e) to U.S. Provisional Application Ser. No. 61/703,721, filed Sep. 20, 2012, the contents of which are incorporated by reference in its entirety into the present disclosure.

FIELD OF THE DISCLOSURE

The disclosure relates to the quantitation of thyroglobulin. In a particular aspect, the disclosure relates to methods for quantitation of thyroglobulin by mass spectrometry.

BACKGROUND

The following description of the background of the disclosure is provided simply as an aid in understanding the disclosure and is not admitted to describe or constitute prior art to the disclosure.

Thyroglobulin, or Tg, is a large dimeric secretary glycoprotein with a molecular weight of 660 kDa comprised of noncovalently bound homodimers.

Tg molecules exist in several forms. The three major Tg molecule sequences as found in the UniProt Knowledgebase (Swiss-Prot+TrEMBL) are P01266 (Human Thyroglobulin Precursor), P01266-2 (Isoform 2 of P01266), and Q59GF02 (Human Thyroglobulin Variant). (See FIGS. 11, 12, and 13, respectively.)

P01266 is the major variant of P01266 with a length of 2768 AA; P01266-2 is an isoform of P01266 with a length of 2711 AA. P01266-2 varies from P01266 at amino acid positions 1510 to 1567 of Tg; and Q59GF0 is a thyroglobulin fragment with a length of 1574 AA. Q59GF0 contains amino acids from positions 1212 to 2768 of Tg.

Tg can only be produced in the thyroid gland and may be produced by either normal well differentiated benign thyroid cells or thyroid cancer cells. It is the precursor protein for thyroid hormone syntheses and serves as the matrix for thyroid iodine storage. Tg is used by the thyroid gland to produce the thyroid hormones thyroxine (T4) and triiodothyronine (T3). Tg levels in the blood can be used as a tumor marker for differentiated thyroid carcinoma (DTC). A high level of Tg in the blood is not by itself an indicator of thyroid cancer, but persistence of Tg in the blood following surgical removal of the thyroid gland indicates persistence of thyroid tissue. A course of treatment following detection of Tg in the blood following surgical removal of the thyroid gland may include administration of radioiodine to ablate all remaining normal thyroid. Continued persistence of Tg in the blood following ablation of all normal thyroid could indicate that some amount of tumor is still present.

Several methods for quantaition of Tg have been developed. For example Spencer, et al., Thyroid, 1999, 9(5):435-41 and Persoon, et al., Clinical Chem 2006, 52(4):686-691 disclose immunometric, radioimmunometric, and immunochemiluminometric methods for quantitation of Tg. These methods are all subject to methodological problems such as differences in standardization, variability in interassay sensitivity and precision, hook effects, and interference attributable to Tg antibodies. The problem of interference attributable to Tg antibodies is particularly troubling for clinical application of monitoring Tg levels as a tumor marker because up to 20% of thyroid cancer patients have Tg autoantibodies.

SUMMARY

The present disclosure provides methods for quantitation of Tg in a sample by mass spectrometry, including tandem mass spectrometry.

In one aspect, methods are provided for determining the amount of Tg in a test sample that include: (a) subjecting a Tg containing test sample to digestion resulting in creation of Tg peptides; (b) purifying one or more Tg peptides; (c) ionizing one or more Tg peptides; (d) detecting the amount of the Tg peptide ion(s) by mass spectrometry; and (e) relating the amount of detected Tg peptide ion(s) to the amount of Tg in the test sample. A preferred enzyme for preparing Tg peptides is trypsin. A suitable Tg peptide for the method is one that can be evaluated by mass spectrometry and can be sufficiently purified from related peptides that may be generated from proteins other than Tg. An example of one such peptide is peptide T129 (sequence VIFDANAPVAVR; SEQ ID NO: 1) which contains amino acids from positions 1579 to 1590 of Tg, has a molecular weight of about 1,270 Da, and is present in all three isoforms of Tg. See FIG. 4.

Formation of peptide T129 provides a unique trypsin generated peptide for thyroglobulin. Also, creation of peptide T129 from tryptic digestion of Tg should be unaffected by the presence or absence of the Tg antibodies. Thus, measurement of the increase in peptide T129 in a test sample offers a way of quantitating the amount of Tg originally in the test sample free from inference from Tg antibodies.

Any appropriate method may be used to determine the amount of Tg peptide resulting from digestion of Tg in a sample. In the event that a test sample may contain endogenous Tg peptide, steps may be taken to make certain that the endogenous peptide is not confused with peptide generated by digesting Tg in sample. One approach is to remove the endogenous Tg peptide from the sample before digesting Tg. This may done, for example, using a size separation technique. Another approach is to analyze a portion of a test sample according to the claimed methods but excluding the digestion step in order to establish a baseline level for the endogenous peptide in the test sample. In this approach, the once a baseline is determined, it can be subtracted from the post-digestion level of the peptide, the later representing both the endogenous peptide and that generated by digestion.

Because the methods may be applied to complex test samples (particularly body fluids or test samples derived from tissue), steps may be taken to purify Tg in the test sample prior to digestion. This may done, for example, using a size separation technique.

In some embodiments, the methods include generating one or more Tg peptide ions in which at least one of the ions has a mass/charge ratio (m/z) corresponding to that of (singly or multiply charged) peptide T129 ions. In preferred related embodiments, the methods include generating one or more Tg peptide ions in which at least one has m/z of 1272.8±0.5, 636.4±0.5, or 424.3±0.5 (corresponding to singly, doubly, or triply charged peptide T129 ions). In related preferred embodiments, the methods may include generating one or more fragment ions of a Tg peptide ion in which at least one has a m/z of 541.3±0.5, 612.3±0.5, 726.4±0.5, 797.4±0.5, 912.4±0.5, or 1059.5±0.5; preferably one or more of the fragment ions are selected from the group consisting of ions with a m/z of 797.4±0.5, 912.4±0.5, and 1059.5±0.5.

In some embodiments, the purification in step (b) is accomplished with at least one size separation technique. Preferably, size separation techniques may be filtration, LC, or any combination thereof. In certain preferred embodiments, the test sample is a body fluid or tissue. In some embodiments, an additional step is included where a second quantity of the test sample is subjected to steps (b) through (e) in order to establish a baseline level of one or more endogenous Tg peptides. In these embodiments, this baseline level can be subtracted from the amount of Tg peptide ion(s) detected in the test sample to determine the amount of Tg peptide ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weight cut off that allows for retention of Tg above the filter and allows Tg peptides to pass through with the filtrate. In related embodiments, the molecular weight cut-off is about 2 kD to 300 kD; more preferably about 100 kD to 300 kD. In these embodiments, the two filtrations (pre-digestion and step (b)) may be conducted with the same filter.

In a second aspect, methods are provided for determining the amount of Tg in a test sample that include: (a) subjecting a Tg containing test sample to digestion resulting in creation of peptide T129; (b) purifying peptide T129; (c) ionizing peptide T129 to generate a precursor ion with a m/z of 636.4±0.5; (d) fragmenting the peptide T129 precursor ion to form one or more fragment ions in which at least one has a m/z of about 797.4±0.5, 912.4±0.5, or 1059.5±0.5; detecting the amount of peptide T129 precursor ions, one or more fragment ions, or both, by mass spectrometry; and (e) relating the amount of detected ion(s) to the amount of Tg in the test sample. In certain preferred embodiments, the test sample is a body fluid or tissue or tissue. In some embodiments, an additional step is included where a second quantity of the test sample is subjected to steps (b) through (e) in order to establish a baseline level of one or more endogenous peptide T129. In these embodiments, this baseline level can be subtracted from the amount of peptide T129 ion(s) detected in the test sample to determine the amount of peptide T129 ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weight cut off that allows for retention of Tg above the filter and allows Tg peptides to pass through with the filtrate. In related embodiments, the molecular weight cut-off is about 2 kD to 300 kD; more preferably about 100 kD to 300 kD. In these embodiments, the two filtrations (pre-digestion and step (b)) may be conducted with the same filter.

As used herein, the term "purification" or "purifying" does not refer to removing all materials from the sample other than the analyte(s) of interest. Instead, purification refers to a procedure that enriches the amount of one or more analytes of interest relative to one or more other components of the sample. Purification, as used herein, does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

As used herein, the term "about" in reference to quantitative measurements, not including the measurement of mass of an ion, refers to the indicated value plus or minus 10%.

As used herein, the term "substantially all" refers to any proportion greater than 50%, more preferably greater than 60%, more preferably greater than 70%, more preferably greater than 80%, and more preferably greater than 90%.

As used herein, the term "test sample" refers to any sample that may contain Tg. As used herein, the term "body fluid or tissue" means any fluid or tissue that can be isolated from the body of an individual. For example, "body fluid or tissue" may include blood, plasma, serum, bile, saliva, urine, tears, perspiration, and the like. If solid tissue is to be analyzed, it may be processed to release a liquid fraction that could contain any Tg present in the tissue. The liquid fraction can then be subject to the methods described herein.

As used herein, the term "digestion" means proteolytic cleavage of proteins into peptides. Digestion agents may include trypsin, Lyc-C, Arg-R, Asp-N and the like. Digestion is carried out by adding a digestion agent (i.e., an enzyme) to a sample and incubating for some period of time.

As used herein, "Tg" or "Tg molecule" means an intact Tg protein molecule.

As used herein, the term "Tg peptide" means any peptide of 100 amino acids or less that is a fragment of the native Tg. Tg peptides can be endogenous to a test sample or formed as a result of digestion of Tg. Peptide T129 is an example of a Tg peptide formed as a result of trypsin digestion of Tg.

As used herein, the term "size separation technique" means any technique (physical or chemical) that allows for the separation of at least one species from a test sample based on any one or more of molecular weight and shape. Examples of such techniques include, but are not limited to, filtration, chromatography, and certain aspects of mass spectrometry.

As used herein, the term "chromatography" refers to a process in which a chemical mixture carried by a liquid or gas is separated into components as a result of differential distribution of the chemical entities as they flow around, over, and/or through a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "mass spectrometry" or "MS" refers to an analytical technique to identify compounds by their mass. MS refers to methods of filtering, detecting, and measuring ions based on their m/z. MS technology generally includes (1) ionizing the compounds to form charged species (e.g., ions); and (2) detecting the molecular weight of the ions and calculating their m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in positive ion mode" refers to those mass spectrometry methods where positive ions are detected. Similarly, the term "operating in negative ion mode" refers to those mass spectrometry methods where negative ions are detected.

As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample is interacted with a partially ionized gas at a sufficiently high temperature to atomize and ionize most elements As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification" or "LOQ" refers to the point where measurements become quantitatively meaningful. The analyte response at this LOQ is identifiable, discrete and reproducible with a precision of 20% and an accuracy of 80% to 120%.

In certain preferred embodiments of the methods disclosed herein, mass spectrometry is performed in positive ion mode. In certain particularly preferred embodiments of the methods disclosed herein, mass spectrometry is performed using ESI as the method of creating ions from Tg peptides.

In preferred embodiments, the ions from Tg peptide ionization detectable in a mass spectrometer are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of about 636.4±0.5, and the fragment ions have a m/z of 1059.5±0.5, 921.4±0.5, or 797.4±0.5.

In some preferred embodiments, a separately detectable internal standard peptide (e.g., T129) is introduced in the test sample after trypsin digestion. In these embodiments, all or a portion of the peptide present in the test sample both from digestion of endogenous Tg and the addition of the internal standard are ionized to produce a plurality of ions detectable in a mass spectrometer, and one or more ions produced from the peptide ionization are detected in a mass spectrometer.

In other preferred embodiments, a separately detectable internal Tg standard is provided in the test sample prior to trypsin digestion. In these embodiments, all or a portion of both the endogenous Tg and the internal standard present in the test sample are digested by trypsin resulting in formation of Tg peptides. Tg peptides are ionized to produce a plurality of ions detectable in a mass spectrometer, and one or more ions produced from Tg peptide ionization are detected by mass spectrometry.

In preferred embodiments, the ions detectable in a mass spectrometer produced from the ionization of Tg peptides resulting from Tg digestion are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of 636.4±0.5, and the fragment ions have a m/z of 1059.5±0.5, 921.4±0.5, 797.4±0.5.

In preferred embodiments, the presence or amount of Tg peptide ions is related to the presence or amount of Tg in the original test sample by comparison to a reference Tg sample.

In one embodiment, the methods involve the combination of LC with mass spectrometry. In another preferred embodiment, the mass spectrometry is tandem mass spectrometry (MS/MS).

The summary of the disclosure described above is non-limiting and other features and advantages of the disclosure will be apparent from the following detailed description of the disclosure, and from the claims.

BRIEF DESCRIPTION OF THE DRAWINGS

FIG. 6 discloses SEQ ID NOS 6-9, respectively, in order of appearance.

FIG. 11 shows the amino acid sequence for P01266 (Human Thyroglobulin Precursor; SEQ ID NO: 3).

FIG. 12 shows the amino acid sequence for P01266-2 (Isoform 2 of P01266; SEQ ID NO: 4).

FIG. 13 shows the amino acid sequence for Q59GF0 (Thyroglobulin Variant-Fragment; SEQ ID NO: 5).

FIGS. 14A through 14G show a comparison of the three sequences contained in FIG. 1-3 demonstrating that they all contain amino acids corresponding to positions 1579 to 1590 of Tg. Sequence P01266 is on top (SEQ ID NO:3); sequence P01266-2 is in the middle (SEQ ID NO:4); and sequence Q59GF0 is at the bottom (SEQ ID NO:5).

DETAILED DESCRIPTION OF THE DISCLOSURE

Figure 1:
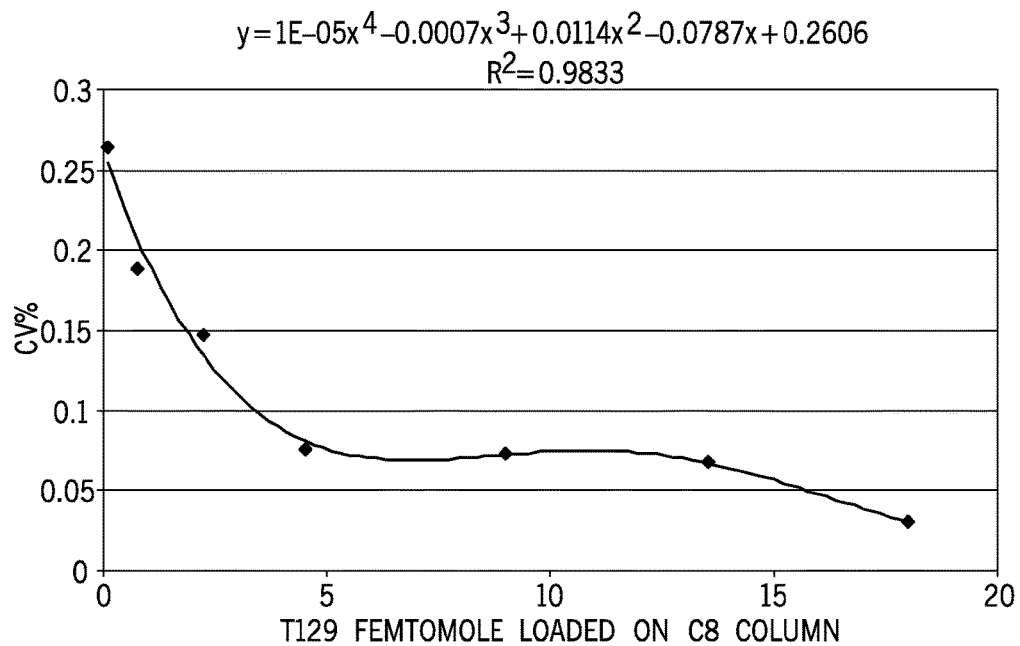
FIG. 1 shows the limit of quantitation verification for Tg peptide ion with m/z corresponding to peptide T129 by MS/MS. Details are described in Example 1.
Figure 2:
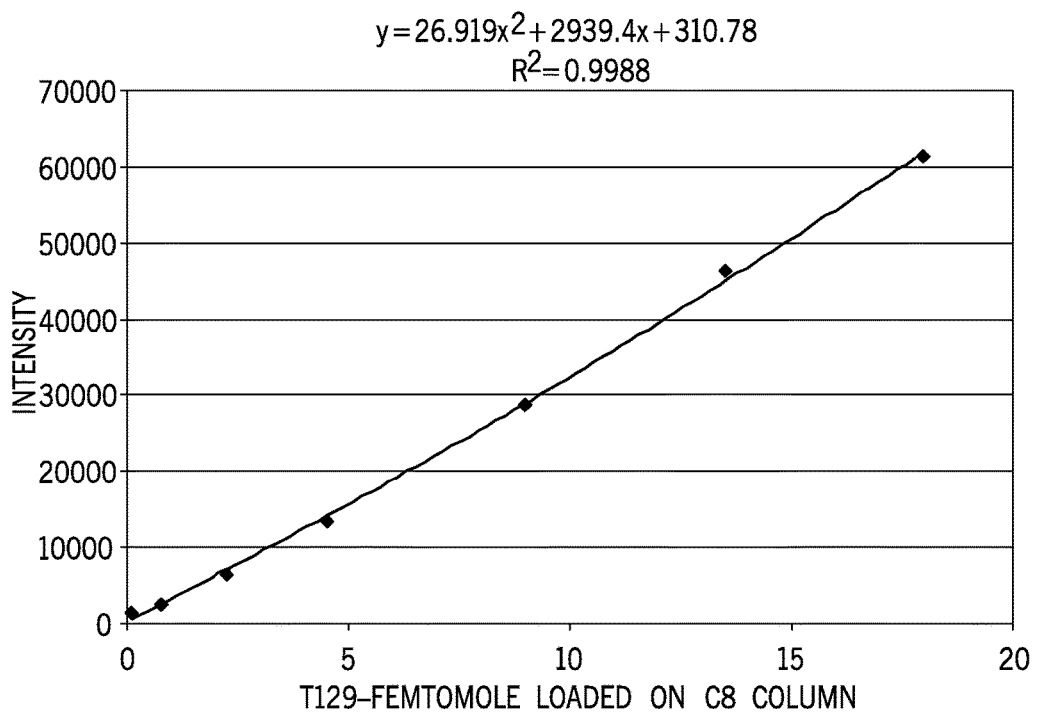
FIG. 2 shows the linearity of the quantitation of peptide T129 in serially diluted stock samples using an LC-MS/MS assay. Details are described in Example 1.
Figure 3:
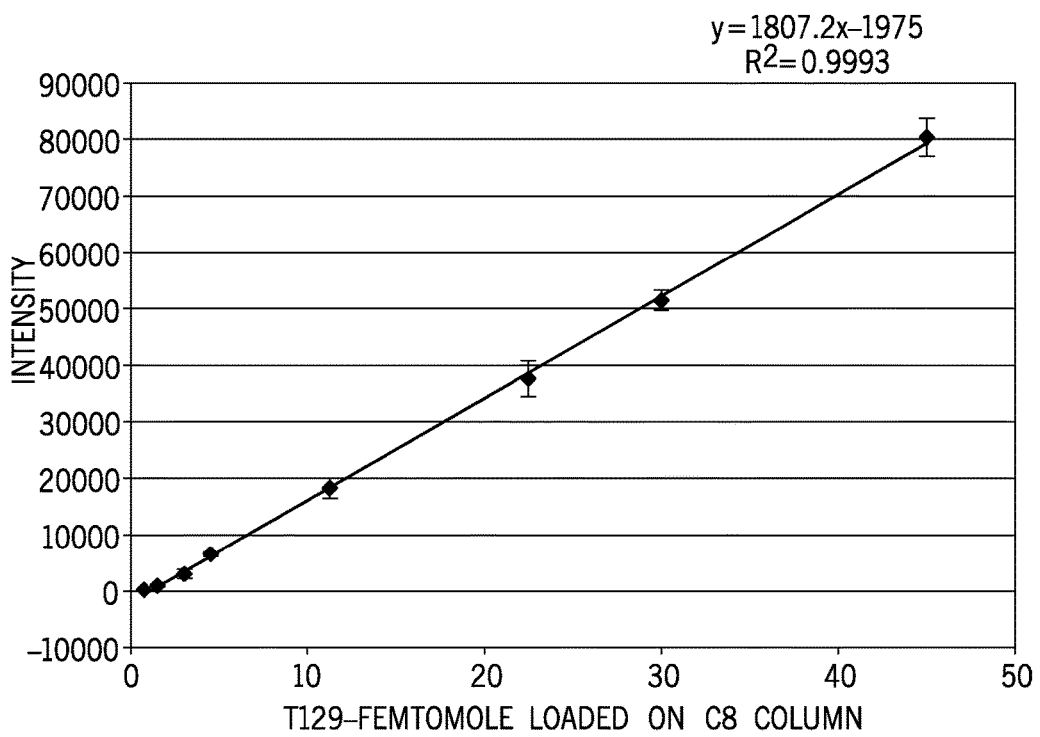
FIG. 3 shows the limit of quantitation verification for peptide T129 in stripped serum by MS/MS. Details are described in Example 2.
Figure 4:
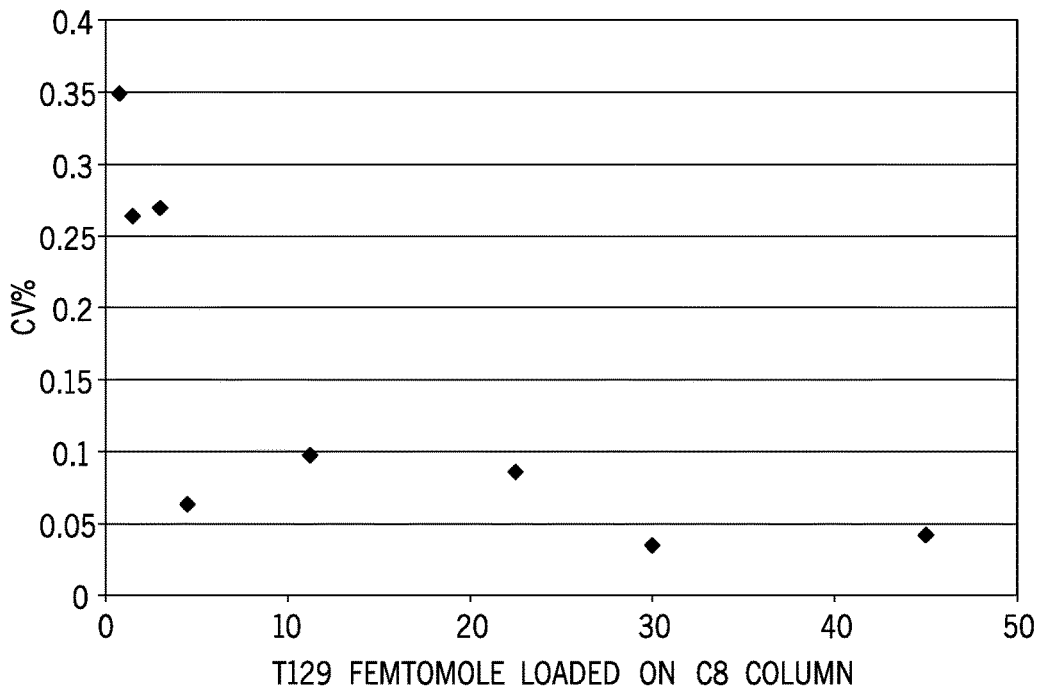
FIG. 4 shows the linearity of the quantitation of peptide T129 in peptide T129 spiked stripped serum using an LC-MS/MS assay. Details are described in Example 2.

Methods are described for quantitatively measuring Tg in a test sample. This quantitative measurement is achieved through the use of LC-MS/MS techniques. Prior to the use of LC-MS/MS, samples may be prepared by the following technique, or any portion thereof. A first purification of Tg in a test sample may be conducted through the use of a size separation technique such that substantially all Tg in the test sample is retained. Following the first purification step, enzymatic digestion of Tg may be carried out creating Tg peptides of interest. After digestion, another utilization of a size separation technique may be employed such that a selected Tg peptide generated in the enzymatic digestion of Tg is purified. This second size separation technique can be used to remove substantially all undigested, higher-molecular weight species. Properly executed, the sample preparation techniques ensure that selected Tg peptides quantitated by LC-MS/MS directly result from enzymatic digestion of Tg originally in the test sample; thus, the level of selected Tg peptides in the test sample at the start of LC-MS/MS is directly proportional to the amount of Tg originally present in the test sample.

Any suitable size separation technique may be utilized, but in the examples that follow, both the first and second size separation techniques are filtration through a molecular weight cut-off filter. It is also possible, as discussed in the Examples that follow, to select a molecular weight cut-off filter with an appropriate molecular weight cut-off such that the same filter can be used for both the first size separation and the second size separation.

LC, most preferably HPLC, is utilized, may be utilized either alone or in combination with other purification methods, to purify selected Tg peptides. This purification is combined with MS/MS, thereby providing an assay system for quantifying selected Tg peptides in a test sample. The quantity of the selected Tg peptides in the test sample is then used to determine the quantity of Tg in the original test sample. The Tg quantitation methods provided herein have enhanced specificity and are less subject to methodological problems (such as Tg antibody interference).

Suitable test samples may include any test sample that may contain the analyte of interest. In some preferred embodiments, a sample is a biological sample; that is, a sample obtained from any biological source, such as an animal, a cell culture, an organ culture, and the like. In certain preferred embodiments, samples are obtained from a mammalian animal, such as a dog, cat, horse, etc. Particularly preferred mammalian animals are primates, most preferably humans. Particularly preferred samples include blood, plasma, serum, urine, saliva, tears, cerebrospinal fluid, or other body fluid or tissue samples. Such samples may be obtained, for example, from a patient; that is, a living person presenting oneself in a clinical setting for diagnosis, prognosis, or treatment of a disease or condition. The test sample is preferably obtained from a patient, for example, serum or plasma.

Sample Preparation for Mass Spectrometry

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, centrifugation, combinations thereof and the like. In certain preferred embodiments, Tg present in a test sample prior to enzymatic digestion.

Filtration is one preferred method of preparing a test sample, especially a biological test sample, such as serum or plasma, for chromatography. Such filtration is carried out by filtering a test sample through a molecular weight cut-off filter to separate species with molecular weights higher than the filter's cut-off (including Tg) from those with molecular weights lower than the filter's cut-off. The test sample remaining above the filter following complete (or near complete) filtration is substantially free of potentially interfering species with molecular weights lower than the filter's cut-off.

The pH of the test sample may then be adjusted to any point required by a digestion agent. In certain preferred embodiments, the digestion agent is trypsin and pH can be adjusted with a solution of ammonium acetate to have a pH suitable for this enzyme. In these preferred embodiments, the sample is then digested with trypsin to form Tg peptides (including peptide T129).

After trypsin digestion, the sample may be purified with a second filtration. This post-digestion filtration can be carried out similarly to the pre-digestion filtration described above (with the exception that the filtrate is retained), in order to separate Tg fragments from potentially interfering species with molecular weights higher than the filter's cut-off that may also be present in the sample. The filtrate from this post-digestion filtration can then be purified by liquid chromatography and subsequently subjected to mass spectrometry analysis.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art may select HPLC instruments and columns that are suitable for use in the methods. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-8 bonded groups. The chromatographic column includes an inlet port for receiving a sample and an outlet port for discharging an effluent that includes the fractionated sample.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one embodiment, the sample to be analyzed is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytypic (i.e. mixed) mode. In preferred embodiments, HPLC is performed on an analytical HPLC system with a C8 solid phase using 0.2% formic acid in HPLC Grade Ultra Pure Water and 0.2% formic acid in 100% methanol as the mobile phases.

Numerous column packings are available for chromatographic separation of samples and selection of an appropriate separation protocol is an empirical process that depends on the sample characteristics, analyte of interest, presence of interfering substances and their characteristics, etc. Commercially available HPLC columns include, but are not limited to, polar, ion exchange (both cation and anion), hydrophobic interaction, phenyl, C-2, C-8, C-18, and polar coating on porous polymer columns.

In one embodiment, the HPLC column has a C8 solid phase with a median particle size of 5 μm (nominal) and a median particle pore size of 100 Å. In a preferred embodiment the column dimensions are 1.0 mm ID×50 mm length (Phenomenex Corp. Luna 5μ C8(2) 100 Å New Column 50×1.0 mm, Phenomenex Cat. No. 00B-4249-A0 or equivalent).

During chromatography, the separation of materials is effected by variables such as choice of eluent (also known as a "mobile phase"), choice of gradient elution and the gradient conditions, temperature, etc.

Detection and Quantitation by Mass Spectrometry

In various embodiments, Tg peptides may be ionized by any method known to the skilled artisan. Mass spectrometry is performed using a mass spectrometer, which includes an ion source for ionizing the fractionated sample and creating charged molecules for further analysis. Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, Tg peptides are ionized by electrospray ionization (ESI) creating Tg peptide precursor ions. In related preferred embodiments, Tg peptide precursor ions are in a gaseous state and the inert collision gas is argon.

After the sample has been ionized, the positively charged ions thereby created may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). In preferred embodiments, ions are detected using SRM.

Preferably, m/z is determined using a quadrupole instrument. In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps may be combined in methods known as "MS/MS". Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 400 to 1600 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of Tg. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the LC purification and mass spectrometry steps may be performed in an on-line fashion.

In certain embodiments, techniques such as MS/MS are used to isolate precursor ions for further fragmentation. In these embodiments, collision activation dissociation (CAD) may be used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy. In alternative embodiments, electron transfer dissociation (ETD) may be used to generate the fragment ions. In ETD, radical anions are used to transfer electrons to multiply charged peptide or protein cations resulting in random cleavage along the peptide backbone.

In particularly preferred embodiments, Tg is detected and/or quantified using LC-MS/MS as follows. A Tg peptide enriched test sample prepared as described above is subjected to LC. The flow of liquid solvent from the chromatographic column enters the heated nebulizer interface of a LC-MS/MS analyzer and the solvent/analyte mixture is converted to vapor in the heated tubing of the interface. The analyte (e.g., Tg peptides), contained in the nebulized solvent, is ionized by the corona discharge needle of the interface, which applies a large voltage to the nebulized solvent/analyte mixture. The ions (i.e. Tg peptide precursor ions) pass through the orifice of the instrument and enter the first quadrupole. Quadrupoles 1 and 3 (Q1 and Q3) are mass filters, allowing selection of ions (i.e., "precursor" and "fragment" ions) based on their m/z. Quadrupole 2 (Q2) is the collision cell, where ions are fragmented. Q1 selects for ions with m/z of peptide T129 precursor ions (m/z of 636.4±0.5). Selected precursor ions are allowed to pass into the collision chamber (Q2), while ions with any other m/z collide with the sides of Q1 and are eliminated. Precursor ions entering Q2 may be fragmented with collision activated dissociation (CAD) through collisions with neutral argon gas molecules. Alternatively, if the precursor ions entering Q2 are multiply charged cations, they may be fragmented with electron transfer dissociation (ETD). The fragment ions generated are passed into Q3, where selected fragment ions are collected while other ions are eliminated.

Using standard methods well known in the art, one of ordinary skill is capable of identifying one or more fragment ions of a particular Tg peptide precursor ion that may be used for selection in Q3. A specific fragment ion is one that will not be formed in significant amounts by other molecules with similar molecular structures. In contrast, a non-specific fragment ion is one that is formed by molecules other than the desired analyte. Suitable specific fragment ions can be identified by testing various molecular standards to determine whether fragment ions formed by a selected Tg peptide are also formed by other molecules with similar structures or features. Preferably, at least one fragment ion specific for Tg peptide ions with m/z corresponding to that of peptide T129 ions are identified. More preferably, one or more of these fragment ions have m/z of 797.4±0.5, 912.4±0.5 or 1059.5±0.5.

As ions collide with the detector they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of Tg peptides with m/z corresponding to peptide T129. As described above, the relative abundance of a given ion may be converted into an absolute amount of the original analyte using calibration standard curves based on peaks of one or more ions of an internal molecular standard. The absolute amount of an analyte detected by LC-MS/MS can then be converted into an absolute amount of Tg that was present in the original test sample.

System Calibration with a Labeled Thyroglobulin Peptide Standard

Incomplete digestion of the thyroglobulin can cause inaccuracy of thyroglobulin quantitation. In some embodiments, a thyroglobulin peptide standard can be added to a test sample prior to digestion. The thyroglobulin peptide standard, in some embodiments, produces one or more Tg peptides that are the same as those produced by thyroglobulin, when digested. In some aspects, the amount of the thyroglobulin peptide standard added to the sample is known.

When the amount of the Tg peptides are quantitated by mass spectrometry, then the rate of digestion can be calculated. In some aspects, the thyroglobulin peptide standard is configured to include the same digestion sites around the Tg peptides so that the digestion rate of the thyroglobulin peptide standard is the same as or similar to that of thyroglobulin. Accordingly, the digestion rate of thyroglobulin is determined, which can be used to calibrate or adjust the quantification of thyroglobulin in the test sample.

In some embodiments, the thyroglobulin peptide standard is shorter than thyroglobulin. In one aspect, the thyroglobulin peptide standard is not longer than about 100 amino acid residues, not longer than about 75 amino acid residues, or not longer than about 70, 60, 50, 40, 30, 25 or 20 amino acid residues long.

In some embodiments, the thyroglobulin peptide standard is digested to form a T129 peptide, or to form a peptide having at least about 70%, 75%, 80%, 85%, 90%, or 95% sequence identity to T129.

In some embodiments, the thyroglobulin peptide standard comprises an amino acid sequence of SEQ ID NO: 2 (KVPESKVIFDANAPVAVRSKVPDS). In some embodiments, the thyroglobulin peptide standard comprises an amino acid sequence having at least about 70%, 75%, 80%, 85%, 90%, or 95% sequence identity SEQ ID NO: 2 (KVPESKVIFDANAPVAVRSKVPDS) but and can form a T129 peptide upon digestion. In some embodiment, the digestion is trypsin digestion.

In some embodiments, one or more residues of the thyroglobulin peptide standard are isotopically labeled, for instance, with $^{13}C$, $^{15}N$, or both. In some embodiments, the labeled amino acid residues are valine residues. In some embodiments, the thyroglobulin peptide standard comprises KVPESKVIFDANAPV*AV*RSKVPDS (SEQ ID NO:6) which, upon trypsin digestion, produces K, VPESK (SEQ ID NO:7), VIFDANAPV*AV*R (SEQ ID NO:8) (T-129-IS1), SK and VPDS (SEQ ID NO:9).

The following examples serve to illustrate the disclosure. These examples are in no way intended to limit the scope of the methods.

EXAMPLES

Example 1: Demonstration of MS Quantitation of Peptide T129

Several samples with various known concentrations of peptide T129 were prepared by series dilution starting with a sample of known peptide T129 concentration. Peptide T129 LOQ and calibration curves were developed from LC-MS/MS analysis of these samples.

LC was performed with a Phenomenex analytical column (Phenomenex Corp. Luna 5μ C8(2) 100 Å New Column 50×1.0 mm). A binary HPLC eluent composed of 0.2% formic acid in ultra pure water (HPLC grade) (mobile phase A) and 0.2% formic acid in 100% methanol (mobile phase B) was applied to the analytical column to separate selected Tg peptides from other species contained in the sample. The binary eluent was applied according to the following gradient profile: as a first step, an 80/20 mixture of mobile phase A/mobile phase B was applied for 120 seconds; as a second step, a 30/70 mixture of mobile phase A/mobile phase B was applied for 60 seconds; as a third step, the relative amount of mobile phase B in the mixture was ramped to a 5/95 mixture of mobile phase A/mobile phase B over a period of 120 seconds; as a fourth step, a 5/95 mixture of mobile phase A/mobile phase B was applied for 60 seconds; as a fifth and final step, an 80/20 mixture of mobile phase A/mobile phase B was applied for 240 seconds.

The separated sample was then subjected to MS/MS for quantitation of one or more Tg peptides with m/z corresponding to peptide T129.

MS/MS was performed using a Finnigan TSQ Quantum Ultra MS/MS system (Thermo Electron Corporation). The following software programs all from ThermoElectron were used in the Examples described herein: Tune Master V 1.2 or newer, Xcalibur V 2.0 SR1 or newer, TSQ Quantum 1.4 or newer, LCQuan V 2.0 or newer, and XReport 1.0 or newer. Liquid solvent/analyte exiting the analytical HPLC column flowed to the heated nebulizer interface of a Thermo Finnigan MS/MS analyzer. The solvent/analyte mixture was converted to vapor in the heated tubing of the interface. Analytes in the nebulized solvent were ionized by the corona discharge needle of the interface, which applied voltage to the nebulized solvent/analyte mixture.

Ions passed to the first quadrupole (Q1), which selected ions with a m/z of 636.4±0.5. Ions entering Quadrupole 2 (Q2) collided with argon gas to generate ion fragments, which were passed to quadrupole 3 (Q3) for further selection. Mass transitions used for quantitation of precursor ions with m/z corresponding to peptide T129 during validation on positive polarity are shown in Table 1.

TABLE 1

Mass transitions for precursor ions with m/z corresponding to peptide T129 (Positive Polarity)

| Precursor Ion (m/z) | Fragment Ion (m/z) |
|---|---|
| 636.4 ± 0.5 | 797.4 ± 0.5, 912.4 ± 0.5 & 1059.5 ± 0.5 |

To determine the limit of quantitation (LOQ) with a precision of 20% and an accuracy of 80% to 120%, seven different samples at varying concentrations were assayed and the reproducibility (CV) determined for each. The LOQ for one or more Tg peptides with m/z corresponding to peptide T129 was defined at about 67 amol/μl.

Figure 5:
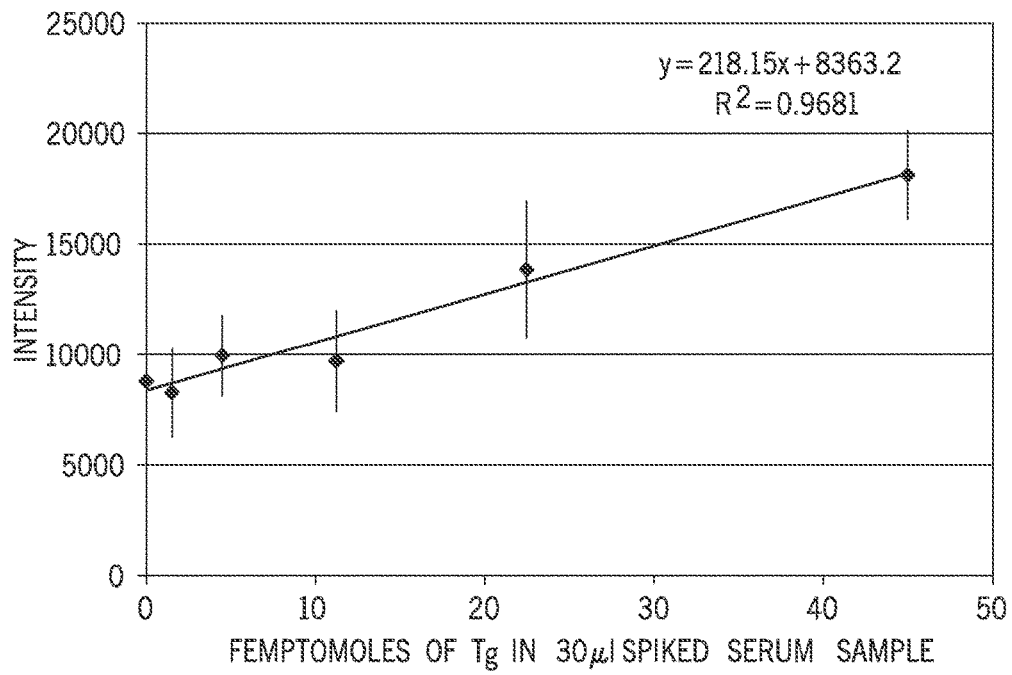
FIG. 5 shows the linearity of the quantitation of Tg peptide ions with m/z corresponding to peptide T129 using an LC-MS/MS assay in stripped serum spiked with Tg prior to processing and concentration according to the methods described herein. Details are described in Example 3.
Figure 6:
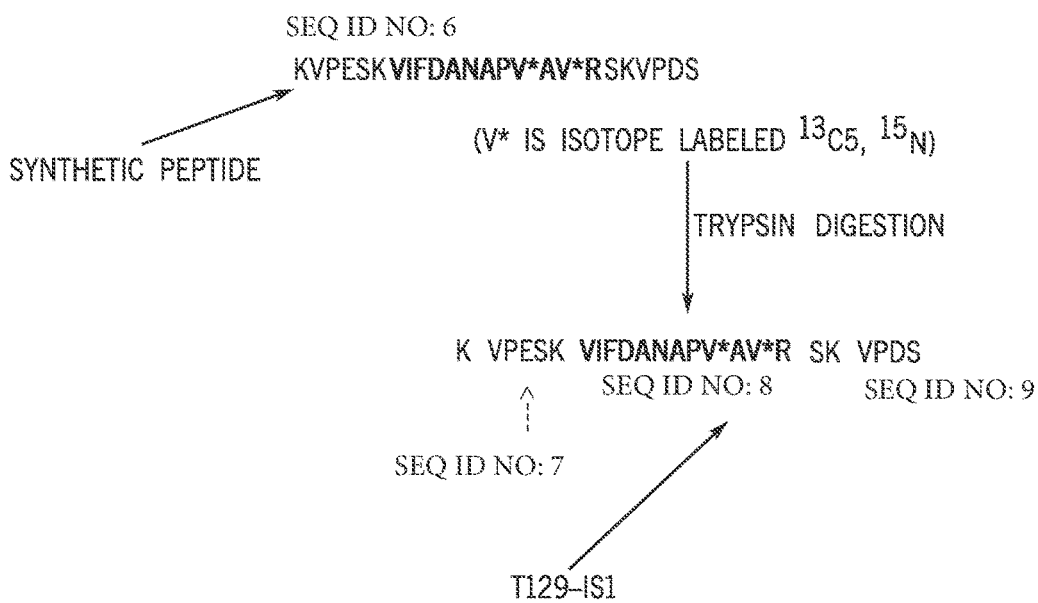
FIG. 6 shows an illustrative embodiment of an isotopically labeled thyroglobulin peptide standard for use as an internal standard as described in Example 4.

Data collected and used to develop the LOQ and Calibration curves in FIGS. 5 and 6 is shown in Table 2.

TABLE 2

Data collected and used to develop LOQ and Calibration curves for peptide T129 in spiked stripped serum samples

| Peptide T129 Concentration (Attomoles/μl) | Femtomoles of peptide T129 in 30 μl sample | Average Ion Counts per Second | CV (%) |
|---|---|---|---|
| 2.5 | 0.075 | 1471.6 | 0.264429 |
| 25 | 0.75 | 2435.6 | 0.188653 |
| 75 | 2.25 | 6455.4 | 0.147946 |
| 150 | 4.5 | 13322.4 | 0.075327 |
| 300 | 9 | 28805 | 0.073374 |
| 450 | 13.5 | 46199.6 | 0.067088 |
| 600 | 18 | 61302.2 | 0.030893 |

Example 2: Demonstration of Quantitation of Peptide T129 in Peptide T129 Spiked Processed, Concentrated and Digested Stripped Serum A 500 μl sample of stripped serum (e.g., the test sample in this Example) was added atop the filter element of a commercially available 300 kDa molecular weight cut-off filter cartridge (Pall Corp. Nanosep 300 kDa, Pall Corp. Cat. No. OD300C33).

The test sample was completely filtered upon centrifugation of the cartridge at 13 kg for 6 minutes. The filtrate was removed and discarded. 500 μl of HPLC grade water was then added to the top of the filter and the cartridge was again centrifuged at 13 kg for 6 minutes. The filtrate was again removed and discarded. Next, 200 μl of 20 mM ammonium acetate was added to the top of the filter. The cartridge was again centrifuged at 13 kg for 3 minutes. The filtrate was again removed and discarded and 100 μl of 20 mM ammonium acetate was added to the top of the filter.

Then, 15 μg of trypsin (Promega Trypsin Gold, Mass Spec Grade, Promega Corp. Cat. No. V5280 or equivalent) was added to the test sample remaining on top of the filter. The resulting mixture was incubated without removal from the filter cartridge at 37 C for up to 17 hours.

After incubation, the filter cartridge was centrifuged at 13 kg for 6 minutes, and the filtrate retained. The filter cartridge was then washed by adding 50 μl of 20 mM ammonium acetate to the top of the filter and centrifuged at 13 kg for 6 minutes. Test samples for analysis by LC-MS/MS were created by pooling the two retained post-digestion filtrates.

The starting volume of stripped serum samples subjected to the above processing and concentration was about 500 μl. The final volume of each pooled post-digestion filtrate was about 130 μl. Thus the above process concentrates samples by a factor of 3.83.

Peptide T129 was then added to the pooled post-digestion filtrates in varying concentrations. 30 μl samples were then analyzed for quantitation of peptide T129 by LC-MS/MS according to the procedure described in Example 1 with the exception that the mass transitions shown in Table 3 were used. The fragment ion with a m/z of 797.4±0.5 was not used due to increased background generated by the processed, concentrated stripped serum.

TABLE 3

Mass transitions for precursor ions with m/z corresponding to peptide T129 from peptide T129 spiked stripped serum samples (Positive Polarity)

| Precursor Ion (m/z) | Fragment Ion (m/z) |
|---|---|
| 636.4 ± 0.5 | 912.4 ± 0.5 & 1059.5 ± 0.5 |

Figure 7:
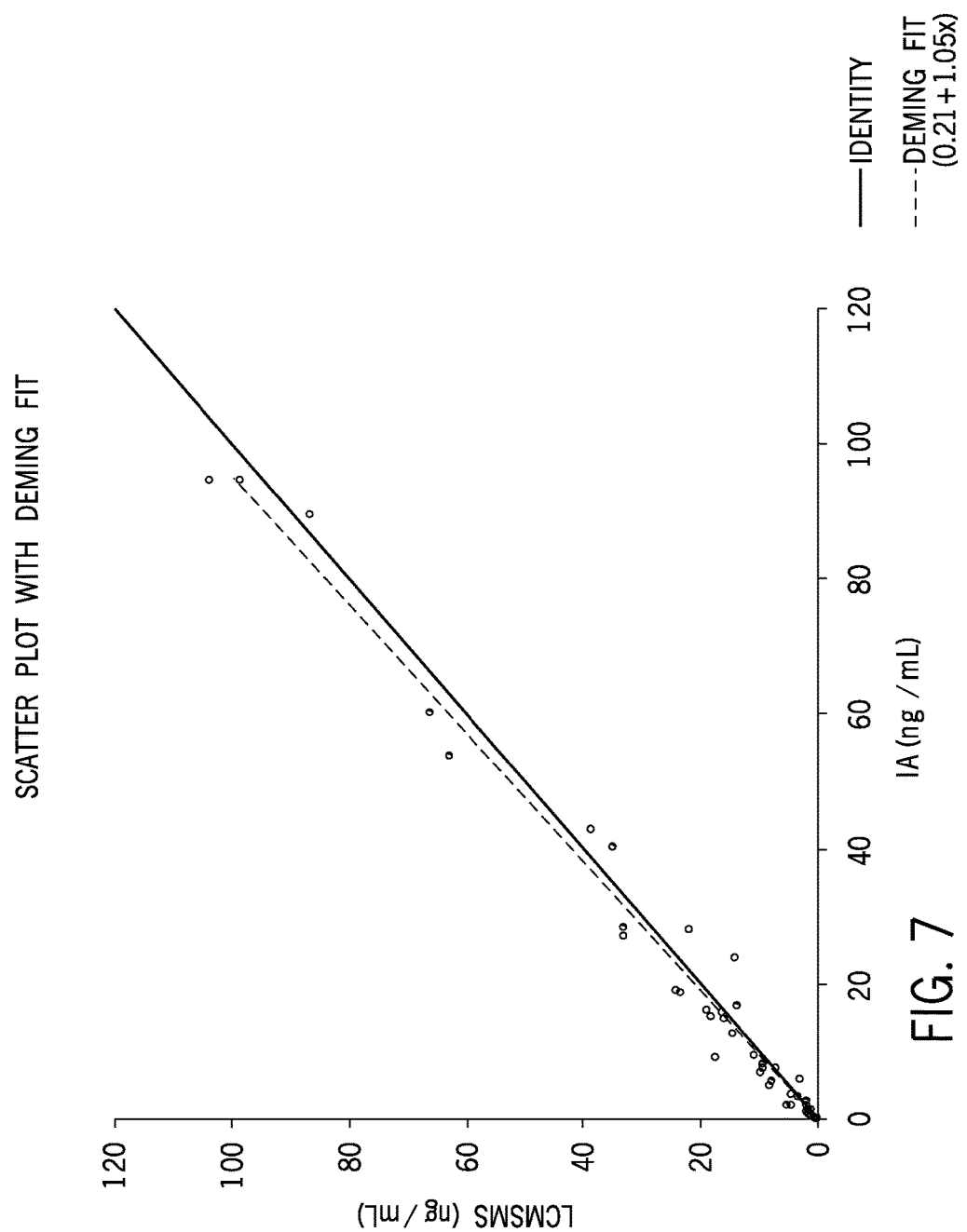
FIG. 7-10 show graphs of thyroglobulin quantitation in test samples by methods of the present technology (Y-axis) versus quantitation by immunoassay or radioimmunoassay (X-axis) from antibody-negative patient discards (FIG. 7, 9) and antibody-positive patient discards (FIG. 8, 10) as described in Example 5.
Figure 8:
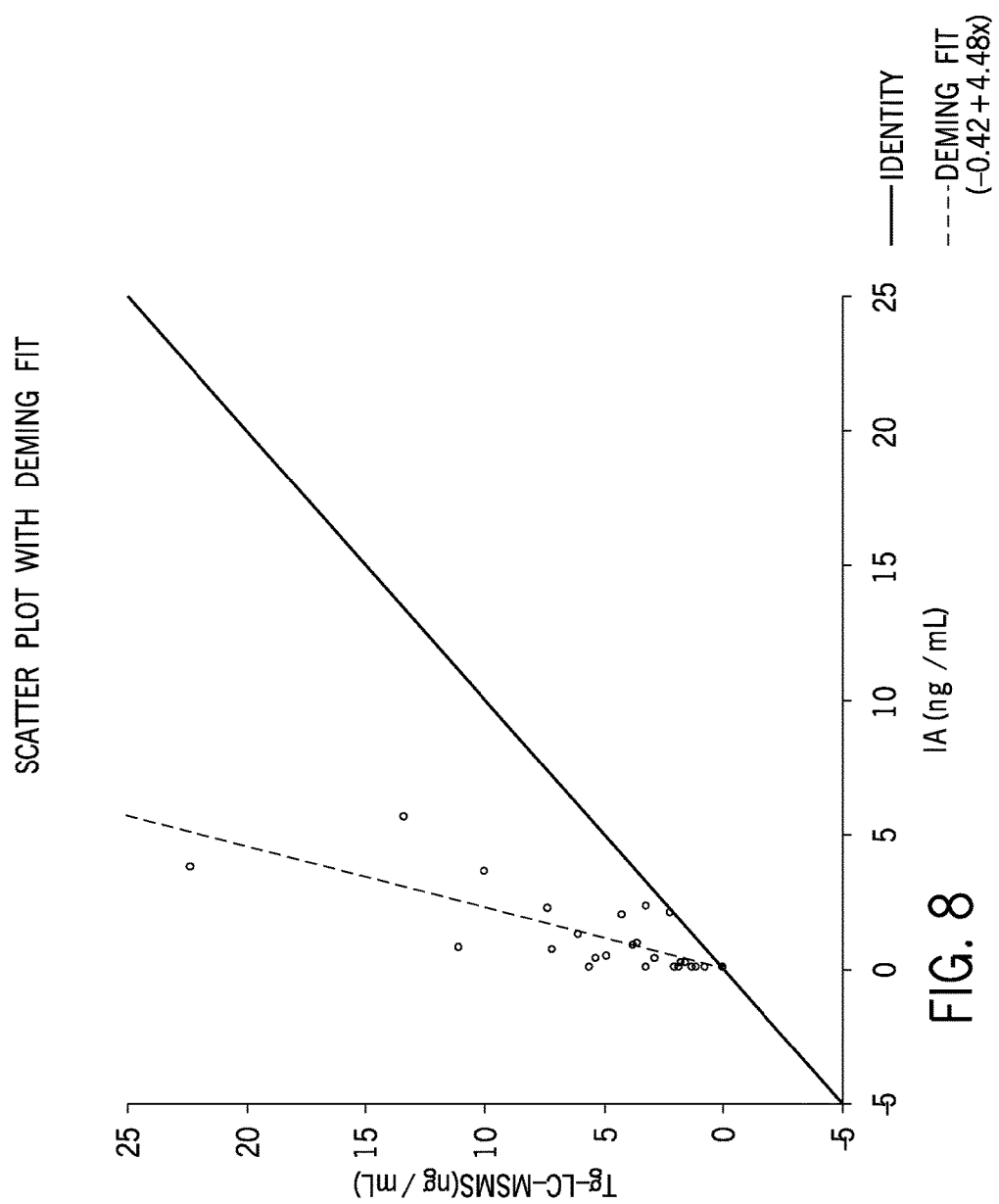

Data collected and used to develop the LOQ and Calibration curves found in FIGS. 7 and 8 is shown in Table 4.

TABLE 4

Data collected and used to develop LOQ and Calibration curves for peptide T129

| Femtomoles of Tg in spiked serum sample | Average Ion Counts per Second | CV (%) |
|---|---|---|
| 0.75 | 203 | 0.348839 |
| 1.5 | 957.25 | 0.263782 |
| 3 | 2984.75 | 0.269659 |
| 4.5 | 6504.75 | 0.063318 |
| 11.25 | 18210.5 | 0.097296 |
| 22.5 | 37620 | 0.085823 |
| 30 | 51451 | 0.035083 |

Example 3: Demonstration of Quantitation of Peptide T129 in Stripped Serum Containing Various Concentrations of Added Tg Several 500 μl samples of stripped serum containing various concentrations of added Tg were prepared according to the procedure detailed in Example 2. LC-MS/MS of the resulting test samples was carried out following the steps detailed in Example 1.

Figure 9:
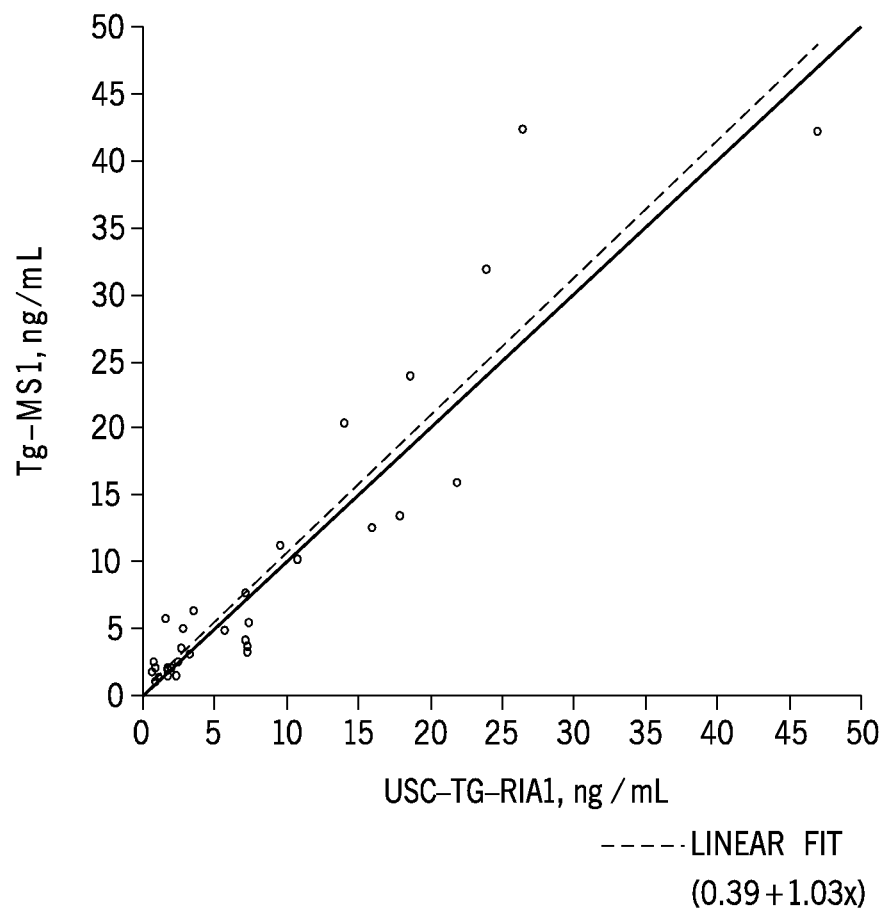
Figure 10:
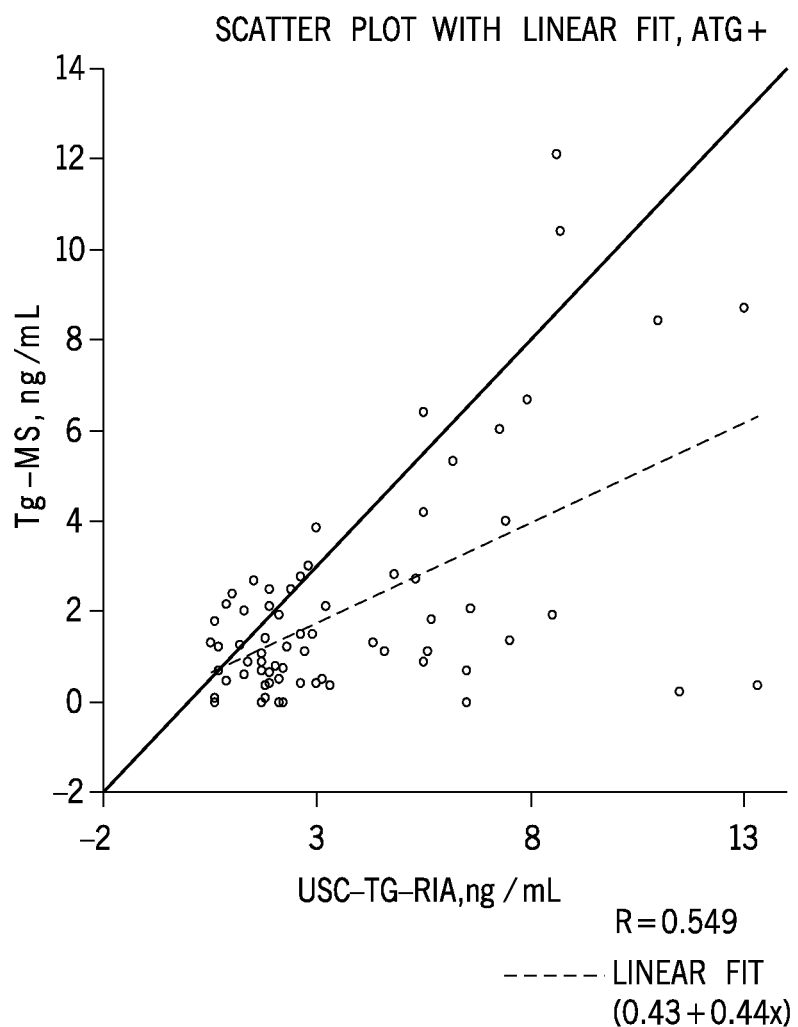

Data collected and used to develop the calibration curve found in FIG. 9 are found in Table 5.

TABLE 5

Data collected and used to develop the calibration curve for peptide T129 MS/MS in Tg spiked stripped serum (processed and condensed as described in Example 3).

| Femtomoles of Tg in spiked serum sample | Average Ion Counts per Second | CV (%) |
|---|---|---|
| 0 | 8784.667 | 0.176987 |
| 1.5 | 8259.5 | 0.246833 |
| 4.5 | 9953.25 | 0.186588 |
| 11.25 | 9696.25 | 0.23816 |
| 22.5 | 13848.25 | 0.225496 |
| 45 | 18125.5 | 0.110826 |

Example 4: Procedure to Confirm Extent of Tg Digestion

To confirm good Tg digestion a synthetic "winged" peptide, which must be digested to liberate an isotopically labeled T-129 internal standard, was added to the test sample. Ideally, a fully labeled Tg would be used that could be added to the serum sample prior to the preparation process (denature/reduction, alkylation and digestions). However, it is currently impossible to obtain such a labeled Tg protein. Therefore a short Tg peptide was synthesized that contained the isotopically labeled T-129 within it (T129-IS1). T129-IS1 is generated during the processing procedure in the same fashion as T129 from Tg present in the serum sample. It therefore acts as a surrogate to a labeled Tg protein and confirms complete processing of the sample.

An illustrative embodiment of this procedure is illustrated in FIG. 6. Briefly, a peptide of sequence KVPESKVIFDANAPV*AV*RSKVPDS (SEQ ID NO:6), was prepared with isotopically labeled valine at the positions indicated. The valine residues were labeled $^{13}C_5$ and $^{15}N$. The peptide was added to the test samples prior to the tryptic digestion. The following fragments are produced during the digestion: K, VPESK (SEQ ID NO:7), VIFDANAPV*AV*R (SEQ ID NO:8) (T-129-IS1), SK and VPDS (SEQ ID NO:9). The amount of T-129-IS1 is quantitated in the same way as T-129 and allows determination of the extent of T-129 digestion.

Example 5: Comparison of Quantitation of Tg in Antibody Negative and Antibody Positive Patient Samples Tg in patient samples was quantitated using both an immunoassay and the present mass spectrometric methods. As shown in the following tables, results from the tests correlated well for antibody-negative samples, but produced very different results when the patient test sample was antibody-positive. The table below shows that in the presence of significant TgAb concentrations, the amount of Tg detected by immunoassay is low, whereas the amount of Tg determined by LC-MS/MS is higher.

| IA TgAb (IU/mL) | IA Tg (ng/mL) | LC-MS/MS Tg ng/mL | Ratio |
|---|---|---|---|
| 56 | 4.6 | 3.3 | 0.7 |
| 65 | 0.2 | <1 | NA |

-continued

| IA TgAb (IU/mL) | IA Tg (ng/mL) | LC-MS/MS Tg ng/mL | Ratio |
|---|---|---|---|
| 65 | 0.2 | <1 | NA |
| 137 | 0.2 | <1 | NA |
| 218 | 0.2 | <1 | NA |
| 1263 | 0.2 | <1 | NA |
| 133 | 2.2 | 2.2 | 1 |
| 153 | 65.2 | 72.4 | 1.1 |
| 83 | 2.4 | 3.2 | 1.3 |
| 259 | 2.1 | 4.2 | 2 |
| 85 | 5.7 | 13.4 | 2.3 |
| 180 | 3.7 | 10 | 2.7 |
| 220 | 2.3 | 7.4 | 3.2 |
| 223 | 0.2 | 1.8 | 6 |
| 45 | 0.2 | 1.3 | 6.5 |
| 317 | 0.2 | 1.3 | 6.5 |
| 137 | 0.6 | 4.9 | 8.2 |
| 812 | 0.8 | 7.2 | 9 |
| 2565 | 0.2 | 1.9 | 9.4 |
| 81 | 0.2 | 2 | 10.2 |
| 1474 | 0.5 | 5.3 | 10.6 |
| 90 | 0.9 | 11.1 | 12.3 |
| 524 | 0.2 | 3.2 | 16 |
| 218 | 0.2 | 3.2 | 16 |
| 621 | 0.2 | 5.6 | 27.9 |

The following table shows the recovery rate of the quantitation assay measured with spiking standards.

| Spike Amount | Sample Number | TgAb IU/mL | Pre Tg MS, ng/mL | Post-Tg MS, ng/mL | Recovery % |
|---|---|---|---|---|---|
| 10 ng/mL | 1 | 141 | 0.8 | 10.8 | 100 |
| | 2 | 176 | 6.3 | 15.3 | 93.8 |
| | 3 | 469 | 2.6 | 14.5 | 112.3 |
| | 4 | 568 | 2.5 | 14.1 | 108.4 |
| | 5 | 577 | 1 | 11.8 | 107 |
| | Control | <20 | 0.8 | 11.1 | 102.8 |
| 20 ng/mL | 6 | 91 | 0.8 | 21.4 | 102.9 |
| | 7 | 141 | 0.8 | 19.6 | 94.2 |
| | 8 | 176 | 6.6 | 24.4 | 91.7 |
| | 9 | 469 | 0.6 | 24.2 | 117.5 |
| | 10 | 2625 | 14.2 | 38.9 | 113.7 |
| | Control | <20 | 0.8 | 20.6 | 101 |
| Control Spike Average Recovery % | | | | | 101.9 |
| Ab + ve Spike Average Recovery % | | | | | 104.15 |

The following table compares the recovery rate between pre-mix and post-mix experiments.

| | TgAb (a), IU/mL | TgAb (b), IU/mL | RIA ng/mL | LC-MS/MS | Tg ng/mL |
|---|---|---|---|---|---|
| Pre-Mix | 13.5 | 73 | 3.8 | <0.4 | <0.2 |
| | 4.7 | 93 | 4.6 | 2.4 | 1.1 |
| | 13.3 | 164 | 5.1 | 4.6 | 2.3 |
| | 12.8 | 204 | 9.1 | 5.9 | <0.2 |
| Post-Mix | 13.1 | 58 | 12.3 (89%) | 9.5 (95%) | 4.1 (41%) |
| | 4.7 | 105 | 15 (103%) | 11.8 (95%) | 4.3 (39%) |
| | 12.3 | 166 | 13.6 (90%) | 14.2 (97%) | 8.5 (69%) |
| | 12.6 | 190 | 16.7 (87%) | 15.3 (96%) | 2.1 (21%) |

Example 6: Tg Quantitation of Test Sample from Tg Antibody Positive Patient

In the present example, a 37 year old woman presented with DTC—had radical thyroidectomy and radioiodine ablation. The patient was found to be Tg Ab positive. The patient tested on automated ICMA platform with result of 0.2 ng/mL Tg. The sample was sent for RIA testing and resulted in Tg of 15 ng/mL, a contradictory result with the ICMA test. An LC-MS/MS assay of the present technology was performed. The latter assay destroys the interfering antibodies and returns a result of 5.6 ng/mL Tg, suggesting patient requires follow-up and potentially needs further surgery.

The contents of the articles, patents, patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the disclosure is also thereby described in terms of any individual member or subgroup of members of the Markush group.

That which is claimed is:

1. A method for determining the amount of thyroglobulin in a test sample, comprising:
   (a) digesting thyroglobulin (Tg) and an added isotopically labeled thyroglobulin peptide standard in said test sample to form Tg peptides and Tg peptide standard products, wherein the thyroglobulin peptide standard comprises SEQ ID NO: 2 (KVPESKVIFDANAPVA-VRSKVPDS);
   (b) ionizing the Tg peptide and the isotopically labeled internal standard; and
   (c) quantifying the amount of the Tg peptide ion from step (b) by mass spectrometry; wherein the amount of the Tg peptide ion detected is related to the amount of thyroglobulin in said test sample.

2. The method of claim 1, wherein the thyroglobulin peptide standard is less than 50 amino acid residues long.

3. The method of claim 1, wherein the Tg peptide comprises SEQ ID NO: 1.

4. The method of claim 1, wherein the Tg peptide ions produced in step (c) comprise one or more ions selected from the group of ions with a mass/charge ratio of 541.3±0.5, 612.3±0.5, 636.4±0.5, 726.4±0.5, 797.4±0.5, 912.4±0.5, or 1059.5±0.5.

5. The method of claim 1, wherein said ionizing comprises generating a Tg peptide precursor ion with a mass/charge ratio of 636.4±0.5, and generating one or more fragment ions with a mass/charge ratio of 797.4±0.5, 912.4±0.5, or 1059.5±0.5.

6. The method of claim 1, wherein said test sample is body fluid or tissue.

7. The method of claim 1, wherein the method comprises liquid chromatography.

8. The method of claim 1, wherein the method comprises enriching a digested Tg peptide comprising SEQ ID NO: 1.

9. The method of claim 1, wherein the ionization is electrospray ionization (ESI).

10. The method of claim 1, wherein one or more residues of the thyroglobulin peptide standard are isotopically labeled with $^{13}C$, $^{15}N$, or both.

11. The method of claim 1, wherein one or more valine residues of the thyroglobulin peptide standard are isotopically labeled.

* * * * *